(12) United States Patent
Maske et al.

(10) Patent No.: US 12,711,582 B2
(45) Date of Patent: Aug. 18, 2026

(54) METHODS AND SYSTEMS FOR GENERATING CLARIFIED AND ENHANCED INTRAOPERATIVE IMAGING DATA

(71) Applicant: Stryker Corporation, Kalamazoo, MI (US)

(72) Inventors: Sanskruti Maske, Gondia (IN); Jose George, Kollam (IN); Lina Gurevich, Vancouver (CA)

(73) Assignee: Stryker Corporation, Portage, MI (US)

( * ) Notice: Subject to any disclaimer, the term of this patent is extended or adjusted under 35 U.S.C. 154(b) by 599 days.

(21) Appl. No.: 18/048,022

(22) Filed: Oct. 19, 2022

(65) Prior Publication Data

US 2023/0122835 A1 Apr. 20, 2023

Related U.S. Application Data

(60) Provisional application No. 63/257,302, filed on Oct. 19, 2021.

(51) Int. Cl.
*G06T 5/70* (2024.01)
*A61B 1/00* (2006.01)
(Continued)

(52) U.S. Cl.
CPC .......... *G06T 5/70* (2024.01); *A61B 1/000095* (2022.02); *A61B 1/000096* (2022.02); (Continued)

(58) Field of Classification Search
None
See application file for complete search history.

(56) References Cited

U.S. PATENT DOCUMENTS

2016/0335751 A1* 11/2016 Sidar .......................... G06T 5/40
2020/0177806 A1 6/2020 Piponi
2021/0202063 A1* 7/2021 Li .......................... G06V 20/52

FOREIGN PATENT DOCUMENTS

CN 113066026 A 7/2021

OTHER PUBLICATIONS

Venkatesha et al. "Unsupervised smoke to desmoked laparoscopic surgery images using contrast driven Cyclic-DesmokeGAN" Computers in Biology and Medicine vol. 123, Aug. 2020, 103873 (Year: 2020).*

(Continued)

*Primary Examiner* — Randolph I Chu
(74) *Attorney, Agent, or Firm* — Morrison & Foerster LLP

(57) ABSTRACT

The present disclosure relates generally to medical imaging, and more specifically to machine-learning techniques for clarifying and enhancing intraoperative images. The system can receive one or more intraoperative images depicting a biological tissue and smoke; input the one or more intraoperative images into a trained neural network to obtain a clarified image depicting the biological tissue that is less obscured by smoke than at least one of the received one or more intraoperative images; enhance, using an equalization algorithm, contrast in the clarified image to obtain an enhanced clarified intraoperative image; and display, on a display, the enhanced clarified intraoperative image, which can be used for decision making within or outside surgeries.

35 Claims, 15 Drawing Sheets
(3 of 15 Drawing Sheet(s) Filed in Color)

(51) Int. Cl.
*G06T 5/40* (2006.01)
*G06T 7/00* (2017.01)

(52) U.S. Cl.
CPC .............. *A61B 1/0005* (2013.01); *G06T 5/40* (2013.01); *G06T 7/0012* (2013.01); *G06T 2207/10016* (2013.01); *G06T 2207/10024* (2013.01); *G06T 2207/10068* (2013.01); *G06T 2207/20081* (2013.01); *G06T 2207/20084* (2013.01); *G06T 2207/30004* (2013.01); *G06T 2207/30168* (2013.01)

(56) References Cited

OTHER PUBLICATIONS

Chen et al. (May 2020). “De-smokeGCN: Generative Cooperative Networks for Joint Surgical Smoke Detection and Removal,” IEEE Transactions on Medical Imaging 39(5): pp. 1615-1625.

International Preliminary Report on Patentability mailed May 2, 2024, directed to International Application No. PCT/US2022/078391; 8 pages.

International Search Report and Written Opinion mailed Feb. 10, 2023, directed to International Application No. PCT/US2022/078391; 11 pages.

Pan et al. (Mar. 2022). “DeSmoke-LAP: improved unpaired image-to-image translation for desmoking in laparoscopic surgery,” International Journal of Computer Assisted Radiology and Surgery 17; pp. 885-893.

Salazar-Colores et al. (Nov. 2020). “Desmoking Laparoscopy Surgery Images Using an Image-to-Image Translation Guided by an Embedded Dark Channel,” located at https://ieeexplore.ieee.org/document/9261326, (12 pages).

Scher. (Nov. 2017). “Playing with Perlin Noise: Generating Realistic Archipelagos,” located at https://medium.com/@yvanscher/playing-with-perlin-noise-generating-realistic-archipelagos-b59f004d8401, (23 pages).

Tchaka et al. “Chromaticity Based Smoke Removal in Endoscopic Images,” Proceedings SPIE 10133, Medical Imaging 2017: Image Processing, Feb. 11-16, 2017, Orlando, Florida, U.S.; 8 pages.

Wang et al. “Multiscale deep desmoking for laparoscopic surgery,” Proceedings SPIE 10949, Medical Imaging 2019: Image Processing, Mar. 15, 2019, San Diego, California, U.S.; 9 pages.

Wang et al. (Oct. 2018). “Variational based smoke removal in laparoscopic images,” BioMedical Engineering Online, 17(139): 18 pages.

* cited by examiner

METHODS AND SYSTEMS FOR GENERATING CLARIFIED AND ENHANCED INTRAOPERATIVE IMAGING DATA

CROSS-REFERENCE TO RELATED APPLICATIONS

This application claims the benefit of U.S. Provisional Application No. 63/257,302, filed Oct. 19, 2021, the entire contents of which are hereby incorporated by reference herein.

FIELD

The present disclosure relates generally to medical imaging, and more specifically to machine-learning techniques to generate clarified and enhanced intraoperative images of a subject (e.g., to aid a surgery, to aid diagnosis and treatment of diseases).

BACKGROUND

Medical systems, instruments or tools are utilized pre-surgery, during surgery, or post-operatively for various purposes. Some of these medical tools may be used in what are generally termed endoscopic procedures or open field procedures. For example, endoscopy in the medical field allows internal features of the body of a patient to be viewed without the use of traditional, fully invasive surgery. Endoscopic imaging systems incorporate endoscopes to enable a surgeon to view a surgical site, and endoscopic tools enable minimally invasive surgery at the site. Such tools may be shaver-type devices which mechanically cut bone and hard tissue, or radio frequency (RF) probes which are used to remove tissue via ablation or to coagulate tissue to minimize bleeding at the surgical site, for example.

In endoscopic surgery, the endoscope is placed in the body at the location at which it is necessary to perform a surgical procedure. Other surgical instruments, such as the endoscopic tools mentioned above, are also placed in the body at the surgical site. A surgeon views the surgical site through the endoscope in order to manipulate the tools to perform the desired surgical procedure. Some endoscopes are usable along with a camera head for the purpose of processing the images received by the endoscope. An endoscopic camera system typically includes a camera head connected to a camera control unit (CCU) by a cable. The CCU processes input image data received from the image sensor of the camera via the cable and then outputs the image data for display. The resolution and frame rates of endoscopic camera systems are ever increasing and each component of the system must be designed accordingly.

Another type of medical imager that can include a camera head connected to a CCU by a cable is an open-field imager. Open-field imagers can be used to image open surgical fields, such as for visualizing blood flow in vessels and related tissue perfusion during plastic, microsurgical, reconstructive, and gastrointestinal procedures.

During surgical procedures (e.g., minimally invasive surgeries), consistently obtaining high-quality video output from the camera feed is important for ensuring smooth navigation through the anatomical objects. However, tissues may be burnt or cauterized during surgical procedures. The smoke generated by cauterization may be captured by the camera and compromise the quality of the video feed. This would create hurdles for surgeons to properly carry out procedures and pose risk to patients. Thus, it is desirable to develop techniques for generating clarified and enhanced intraoperative imaging data to reduce or eliminate smoke from the imaging data and provide improved visibility.

SUMMARY

Disclosed herein are exemplary devices, apparatuses, systems, methods, and non-transitory storage media for clarifying and enhancing intraoperative images. The systems, devices, and methods may be used for imaging tissue of a subject, such as in endoscopic imaging procedures or open field surgical imaging procedures. Imaging may be performed pre-operatively, intra-operatively, post-operatively, and during diagnostic imaging sessions and procedures. The imaging methods may exclude insertion of an endoscopic imager into a lumen in the body or the use of an open field imaging system. The endoscopic imager may be pre-inserted into a lumen in the body. The imaging methods may exclude an invasive surgical step.

During surgical procedures (e.g., minimally invasive surgeries), consistently obtaining high-quality video output from the camera feed is important for ensuring smooth navigation through the anatomical objects. However, tissues may be burnt or cauterized during surgical procedures. The smoke generated by cauterization may be captured by the camera and compromise the quality of the video feed. This would create hurdles for surgeons to properly carry out procedures and pose risk to patients. Thus, it is desirable to develop techniques for generating clarified and enhanced intraoperative imaging data to reduce or eliminate smoke from the imaging data and provide improved visibility.

Existing approaches for removing or reducing smoke are deficient for a number of reasons. For example, one existing approach involves removing smoke physically by using a suction mechanism through a separate scope inserted inside the body. This approach is invasive and introduces additional complexities in the surgical procedures. Another approach involves using traditional de-smoking algorithms that do not involve machine-learning, but instead solely rely on a contrast enhancer or sharpener to achieve smoke reduction. With these traditional algorithms, a trade off exists between the amount of smoke removed and the image quality with respect to color and structure preservation. For example, these traditional algorithms can introduce color distortion (e.g., color saturating towards grey) and structural visibility loss in the resulting images.

Examples of the present disclosure comprise an end-to-end hybrid approach comprising a machine-learning-based component and a contrast enhancer to automatically remove or reduce smoke present in an image. Examples of the present disclosure can effectively remove smoke while enhancing structural fidelity and preserving color in the resulting images, thus providing improved visibility of the surgical sites for surgeons to carry out surgical procedures. An exemplary system can receive an intraoperative image depicting a biological tissue and smoke (e.g., captured by an endoscopic camera) and input the intraoperative image into a trained neural network to obtain a clarified image depicting the biological tissue that is less obscured by smoke than the received intraoperative image. The system further enhances, using an equalization algorithm (e.g., CLAHE), contrast in the clarified image to obtain an enhanced clarified intraoperative image. The resulting image is a clean and sharp image retaining original color and local structure information.

In some examples, the trained neural network can be configured to obtain a joint estimation of atmospheric light and transmission map, which is then used to obtain the clarified image. In some examples, the trained neural network is a lightweight neural network that can be trained using image pairs, each image pair comprising a smoke-free image and a smoky image. In some examples, the smoky image is a simulated image generated based on the smoke-free image.

The system can display the enhanced clarified intraoperative image. In some examples, the system displays the enhanced clarified intraoperative image as part of an intraoperative video stream to aid the surgical procedure. The enhanced clarified image facilitates smooth navigation by reducing the amount of smoke in the video stream. The techniques described herein can be used in any surgical procedure to provide improved visibility of the surgical site (e.g., cauterizing bleeding blood vessels, removal of polyp, removal of unwanted tissues).

In some examples, the intraoperative image is captured during a surgical procedure, and the system can provide a recommendation related to the surgical procedure based on the enhanced clarified intraoperative image. The recommendation can be related to navigating a surgical instrument. The recommendation can be an indication of an anatomical structure to operate on or to avoid. The recommendation can be related to administration of a particular treatment. The recommendation can be related to identification of a high-risk area or a potential complication. In some examples, the recommendation is provided during the surgery such that the surgeon can alter the course of action in real time. Although the intraoperative image may be captured during a surgical procedure, the imaging methods per se may exclude an invasive surgical step. For instance, the imaging methods may exclude insertion of an endoscopic imager into a lumen in the body or the use of an open field imaging system. The endoscopic imager may be pre-inserted into a lumen in the body.

In some examples, the enhanced clarified image can be provided (e.g., displayed) to a medical practitioner, who can review the image to identify, recommend, and/or administer a treatment or some other course of action to the patient pre-surgery, during surgery, or post-operatively. In some examples, the enhanced clarified image can be provided to a computer-based system, which processes the image to identify, recommend, and/or administer a treatment or some other course of action to the patient. For example, the system can provide the enhanced clarified image to a classification model to automatically identify one or more complications. Based on the identified issue, a treatment or some other course of action can be automatically recommended (e.g., via one or more graphical user interfaces). The treatment can also be automatically administered, for example, by a medical device (e.g., a surgical robot) based on the automatically recommended treatment.

According to some aspects, an exemplary method for clarifying and enhancing intraoperative images comprises: receiving one or more intraoperative images depicting a biological tissue and smoke; inputting the one or more intraoperative images into a trained neural network to obtain a clarified image depicting the biological tissue that is less obscured by smoke than at least one of the one or more received intraoperative images; enhancing, using an equalization algorithm, contrast in the clarified image to obtain an enhanced clarified intraoperative image; and displaying, on a display, the enhanced clarified intraoperative image.

According to some aspects, the received one or more intraoperative images have been captured by an endoscopic camera.

According to some aspects, the received one or more intraoperative images are part of an intraoperative video.

According to some aspects, the trained neural network is a trained convolutional neural network ("CNN").

According to some aspects, the CNN comprises a plurality of layers for optimizing a transmission map and an atmospheric light in an atmospheric scattering equation.

According to some aspects, the trained neural network is trained using a plurality of smoke-free training images and a plurality of simulated training images depicting smoke.

According to some aspects, each simulated training image is generated by: receiving a smoke-free training image of the plurality of smoke-free training images; generating a simulated smoke layer; and aggregating the smoke-free training image and the simulated smoke layer to obtain the simulated training image depicting smoke.

According to some aspects, the simulated smoke layer is generated using Perlin noise.

According to some aspects, aggregating the smoke-free training image and the simulated smoke layer comprises superposing the smoke layer onto the smoke-free image based on a predefined weight.

According to some aspects, the trained neural network is trained using artificial images generated using a GAN; and the GAN is trained using real smoky images as a training seed.

According to some aspects, the equalization algorithm is an Adaptive Histogram Equalization algorithm.

According to some aspects, the equalization algorithm is a Contrast Limited Adaptive Histogram Equalization ("CLAHE") algorithm.

According to some aspects, enhancing the clarified image comprises: converting the clarified image from a RGB color format to a YCbCr color format; applying the CLAHE algorithm to the Y component of the clarified image; and converting the clarified image from the YCbCr format to the RGB color format.

According to some aspects, the CLAHE algorithm is applied based on parameters optimized for endoscopic images using heuristics.

According to some aspects, the trained neural network is trained by: receiving a simulated training image depicting smoke; receiving a smoke-free training image corresponding to the simulated training image; inputting the simulated training image depicting smoke into the trained neural network to obtain a generated image; comparing the generated image with the smoke-free training image; calculating a loss based on the comparison; and updating the trained neural network based on the loss.

According to some aspects, the trained neural network is trained by: receiving a simulated training image depicting smoke; receiving a smoke-free training image corresponding to the simulated training image; enhancing the smoke-free training image using the equalization algorithm to obtain an enhanced smoke-free training image; inputting the simulated training image depicting smoke into the trained neural network to obtain a generated image; enhancing the generated image using the equalization algorithm to obtain an enhanced generated image; calculating a first loss based on the generated image and the smoke-free training image corresponding to the simulated training image; calculating a second loss based on the enhanced smoke-free training image and the enhanced generated image; and updating the trained neural network based on the first loss and the second loss.

According to some aspects, the one or more received intraoperative images are inputted into the trained neural network in accordance with a determination that smoke is detected in the received intraoperative image.

According to some aspects, the method further comprises: determining a smoke level in the received one or more intraoperative images, wherein the trained neural network is selected based on the determined smoke level.

According to some aspects, the method further comprises: providing a navigation recommendation based on the enhanced and clarified intraoperative image.

According to some aspects, an exemplary system for clarifying and enhancing intraoperative images comprises: one or more processors; one or more memories; and one or more programs, wherein the one or more programs are stored in the one or more memories and configured to be executed by the one or more processors, the one or more programs including instructions for: receiving one or more intraoperative images depicting a biological tissue and smoke; inputting the one or more intraoperative images into a trained neural network to obtain a clarified image depicting the biological tissue that is less obscured by smoke than at least one of the one or more received intraoperative images; enhancing, using an equalization algorithm, contrast in the clarified image to obtain an enhanced clarified intraoperative image; and displaying, on a display, the enhanced clarified intraoperative image.

According to some aspects, the received one or more intraoperative images have been captured by an endoscopic camera.

According to some aspects, the received one or more intraoperative images are part of an intraoperative video.

According to some aspects, the trained neural network is a trained convolutional neural network ("CNN").

According to some aspects, the CNN comprises a plurality of layers for optimizing a transmission map and an atmospheric light in an atmospheric scattering equation.

According to some aspects, the trained neural network is trained using a plurality of smoke-free training images and a plurality of simulated training images depicting smoke.

According to some aspects, each simulated training image is generated by: receiving a smoke-free training image of the plurality of smoke-free training images; generating a simulated smoke layer; and aggregating the smoke-free training image and the simulated smoke layer to obtain the simulated training image depicting smoke.

According to some aspects, the simulated smoke layer is generated using Perlin noise.

According to some aspects, aggregating the smoke-free training image and the simulated smoke layer comprises superposing the smoke layer onto the smoke-free image based on a predefined weight.

According to some aspects, the trained neural network is trained using artificial images generated using a GAN; and the GAN is trained using real smoky images as a training seed According to some aspects, the equalization algorithm is an Adaptive Histogram Equalization algorithm.

According to some aspects, the equalization algorithm is a Contrast Limited Adaptive Histogram Equalization ("CLAHE") algorithm.

According to some aspects, enhancing the clarified image comprises: converting the clarified image from a RGB color format to a YCbCr color format; applying the CLAHE algorithm to the Y component of the clarified image; and converting the clarified image from the YCbCr format to the RGB color format.

According to some aspects, the CLAHE algorithm is applied based on parameters optimized for endoscopic images using heuristics.

According to some aspects, the trained neural network is trained by: receiving a simulated training image depicting smoke; receiving a smoke-free training image corresponding to the simulated training image; inputting the simulated training image depicting smoke into the trained neural network to obtain a generated image; comparing the generated image with the smoke-free training image; calculating a loss based on the comparison; and updating the trained neural network based on the loss.

According to some aspects, the trained neural network is trained by: receiving a simulated training image depicting smoke; receiving a smoke-free training image corresponding to the simulated training image; enhancing the smoke-free training image using the equalization algorithm to obtain an enhanced smoke-free training image; inputting the simulated training image depicting smoke into the trained neural network to obtain a generated image; enhancing the generated image using the equalization algorithm to obtain an enhanced generated image; calculating a first loss based on the generated image and the smoke-free training image corresponding to the simulated training image; calculating a second loss based on the enhanced smoke-free training image and the enhanced generated image; and updating the trained neural network based on the first loss and the second loss.

According to some aspects, the received one or more intraoperative images are inputted into the trained neural network in accordance with a determination that smoke is detected in the received intraoperative image.

According to some aspects, the one or more programs further include instructions for: determining a smoke level in the received one or more intraoperative images, wherein the trained neural network is selected based on the determined smoke level.

According to some aspects, the one or more programs further include instructions for: providing a navigation recommendation based on the enhanced and clarified intraoperative image.

An exemplary non-transitory computer-readable storage medium stores one or more programs, the one or more programs comprising instructions, which when executed by one or more processors of an electronic device, cause the electronic device to perform any of the techniques described herein.

An exemplary computer program product comprises instructions which, when executed by one or more processors of an electronic device, cause the electronic device to perform any of the techniques described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described, by way of example only, with reference to the accompanying drawings, in which.

DETAILED DESCRIPTION

Figure 1A:
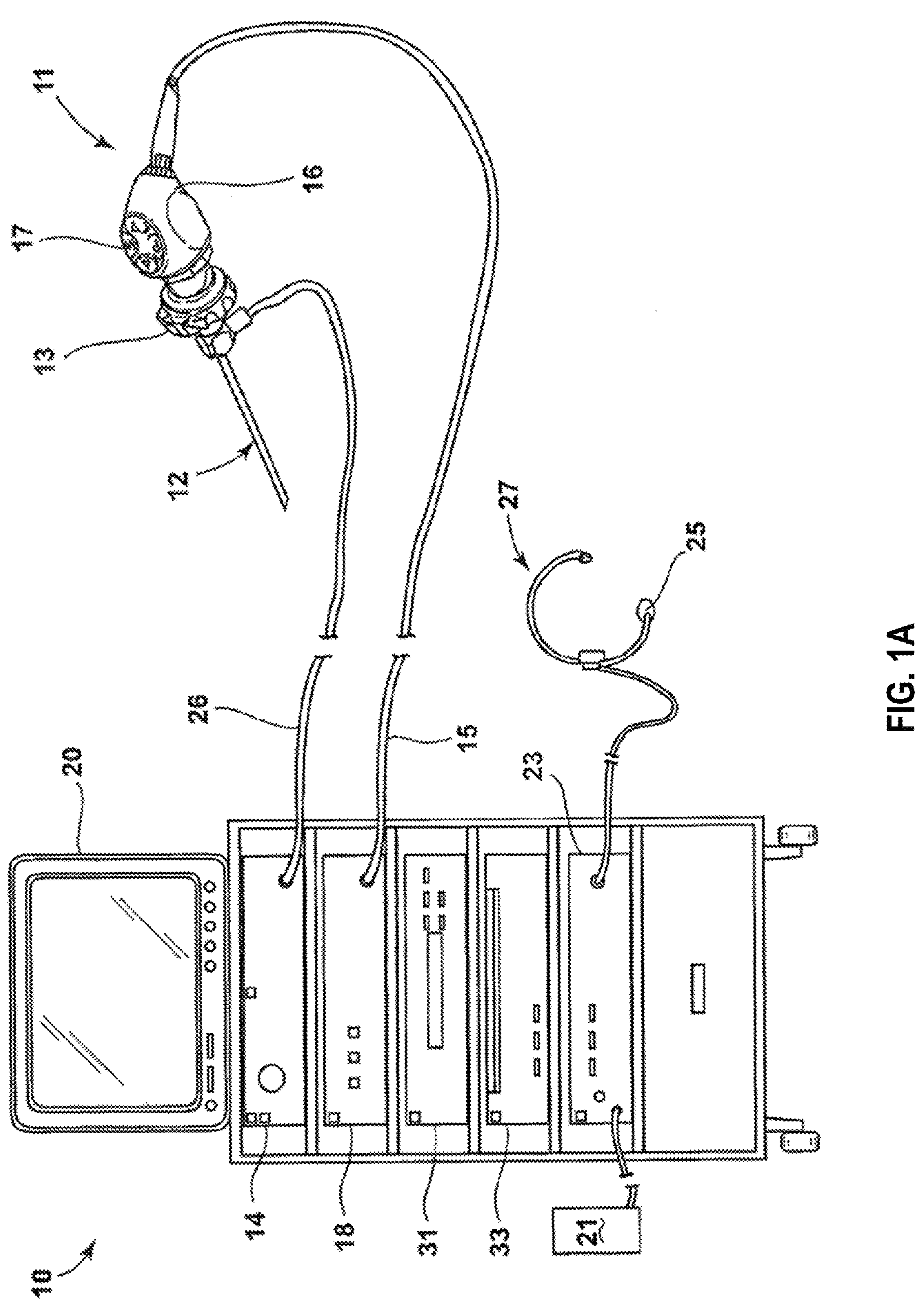
FIG. 1A is an illustration of an endoscopic camera system, according to some examples.

Reference will now be made in detail to implementations and various aspects and variations of systems and methods described herein. Although several exemplary variations of the systems and methods are described herein, other variations of the systems and methods may include aspects of the systems and methods described herein combined in any suitable manner having combinations of all or some of the aspects described. Examples will now be described more fully hereinafter with reference to the accompanying drawings; however, they may be embodied in different forms and should not be construed as limited to the examples set forth herein. Rather, these examples are provided so that this disclosure will be thorough and complete, and will fully convey exemplary implementations to those skilled in the art.

Disclosed herein are exemplary devices, apparatuses, systems, methods, and non-transitory storage media for clarifying and enhancing intraoperative images. The systems, devices, and methods may be used for imaging tissue of a subject, such as in endoscopic imaging procedures or open field surgical imaging procedures. Imaging may be performed pre-operatively, intra-operatively, post-operatively, and during diagnostic imaging sessions and procedures. The imaging methods may exclude insertion of an endoscopic imager into a lumen in the body or the use of an open field imaging system. The endoscopic imager may be pre-inserted into a lumen in the body. The imaging methods may exclude an invasive surgical step.

During surgical procedures (e.g., minimally invasive surgeries), consistently obtaining high-quality video output from the camera feed is important for ensuring smooth navigation through the anatomical objects. However, tissues may be burnt or cauterized during surgical procedures. The smoke generated by cauterization may be captured by the camera and compromise the quality of the video feed. This would create hurdles for surgeons to properly carry out procedures and pose risk to patients. Thus, it is desirable to develop techniques for generating clarified and enhanced intraoperative imaging data to reduce or eliminate smoke from the imaging data and provide improved visibility.

Existing approaches for removing or reducing smoke are deficient for a number of reasons. For example, one existing approach involves removing smoke physically by using a suction mechanism through a separate scope inserted inside the body. This approach is invasive and introduces additional complexities in the surgical procedures. Another approach involves using traditional de-smoking algorithms that do not involve machine-learning, but instead solely rely on a contrast enhancer or sharpener to achieve smoke reduction. With these traditional algorithms, a trade off exists between the amount of smoke removed and the image quality with respect to color and structure preservation. For example, these traditional algorithms can introduce color distortion (e.g., color saturating towards grey) and structural visibility loss in the resulting images.

Examples of the present disclosure comprise an end-to-end hybrid approach comprising a machine-learning-based component and a contrast enhancer to automatically remove or reduce smoke present in an image. Examples of the present disclosure can effectively remove smoke while enhancing structural fidelity and preserving color in the resulting images, thus providing improved visibility of the surgical sites for surgeons to carry out surgical procedures. An exemplary system can receive an intraoperative image depicting a biological tissue and smoke (e.g., captured by an endoscopic camera) and input the intraoperative image into a trained neural network to obtain a clarified image depicting the biological tissue that is less obscured by smoke than the received intraoperative image. The system further enhances, using an equalization algorithm (e.g., CLAHE), contrast in the clarified image to obtain an enhanced clarified intraoperative image. The resulting image is a clean and sharp image retaining original color and local structure information.

In some examples, the trained neural network can be configured to obtain a joint estimation of atmospheric light and transmission map, which is then used to obtain the clarified image. In some examples, the trained neural network is a lightweight neural network that can be trained using image pairs, each image pair comprising a smoke-free image and a smoky image. The lightweight neural network can be deployed on lighter hardware and requires less computation. In such examples, the lightweight design of the trained neural network, such as described below, enables the network to be used in a real-time surgical imaging workflow by allowing for practical real-time implementation in a surgical imaging hardware environment (e.g., one or more of an FPGA, GPU, TPU, IPU, or other processing hardware). In some examples, the smoky image is a simulated image generated based on the smoke-free image.

The system can display the enhanced clarified intraoperative image. In some examples, the system displays the enhanced clarified intraoperative image as part of an intraoperative video stream to aid the surgical procedure. The enhanced clarified image facilitates smooth navigation by reducing the amount of smoke in the video stream. The techniques described herein can be used in any surgical procedure to provide improved visibility of the surgical site (e.g., cauterizing bleeding blood vessels, removal of polyp, removal of unwanted tissues).

In some examples, the intraoperative image is captured during a surgical procedure, and the system can provide a recommendation related to the surgical procedure based on the enhanced clarified intraoperative image. The recommendation can be related to navigating a surgical instrument. The recommendation can be an indication of an anatomical structure to operate on or to avoid. The recommendation can be related to administration of a particular treatment. The recommendation can be related to identification of a high-risk area or a potential complication. In some examples, the recommendation is provided during the surgery such that the surgeon or a surgical robot can alter the course of action in real time.

In some examples, the enhanced clarified image can be provided (e.g., displayed) to a medical practitioner, who can review the image to identify, recommend, and/or administer a treatment or some other course of action to the patient pre-surgery, during surgery, or post-operatively. In some examples, the enhanced clarified image can be provided to a computer-based system, which processes the image to identify, recommend, and/or administer a treatment or some other course of action to the patient. For example, the system can provide the enhanced clarified image to a classification model to automatically identify one or more complications. Based on the identified issue, a treatment or some other course of action can be automatically recommended (e.g., via one or more graphical user interfaces). The treatment can also be automatically administered, for example, by a medical device (e.g., a surgical robot) based on the automatically recommended treatment.

In some examples, the enhanced clarified image can be provided (e.g., displayed) to a medical practitioner, who can review the image to identify, recommend, and/or administer a treatment to the patient pre-surgery, during surgery, or post-operatively. In some examples, the enhanced clarified image can be provided to a computer-based system, which processes the image to identify, recommend, and/or administer a treatment to the patient. For example, the system can provide the enhanced clarified image to a classification model to automatically identify one or more complications. Based on the identified issue, a treatment can be automatically recommended (e.g., via one or more graphical user interfaces). The treatment can also be automatically administered, for example, by a medical device (e.g., a surgical robot) based on the automatically recommended treatment. In the following description, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1A shows an example of an endoscopic imaging system 10, which includes a scope assembly 11 which may be utilized in endoscopic procedures. The scope assembly 11 incorporates an endoscope or scope 12 which is coupled to a camera head 16 by a coupler 13 located at the distal end of the camera head 16. Light is provided to the scope by a light source 14 via a light guide 26, such as a fiber optic cable. The camera head 16 is coupled to a camera control unit (CCU) 18 by an electrical cable 15. The CCU 18 is connected to, and communicates with, the light source 14. Operation of the camera head 16 is controlled, in part, by the CCU 18. The cable 15 conveys video image and/or still image data from the camera head 16 to the CCU 18 and may convey various control signals bi-directionally between the camera head 16 and the CCU 18.

A control or switch arrangement 17 may be provided on the camera head 16 for allowing a user to manually control various functions of the system 10, which may include switching from one imaging mode to another, as discussed further below. Voice commands may be input into a microphone 25 mounted on a headset 27 worn by the practitioner and coupled to the voice-control unit 23. A hand-held control device 29, such as a tablet with a touch screen user interface or a PDA, may be coupled to the voice-control unit 23 as a further control interface. In the illustrated example, a recorder 31 and a printer 33 are also coupled to the CCU 18. Additional devices, such as an image capture and archiving device, may be included in the system 10 and coupled to the CCU 18. Video image data acquired by the camera head 16 and processed by the CCU 18 is converted to images, which can be displayed on a monitor 20, recorded by recorder 31, and/or used to generate static images, hard copies of which can be produced by the printer 33.

Figure 1B:
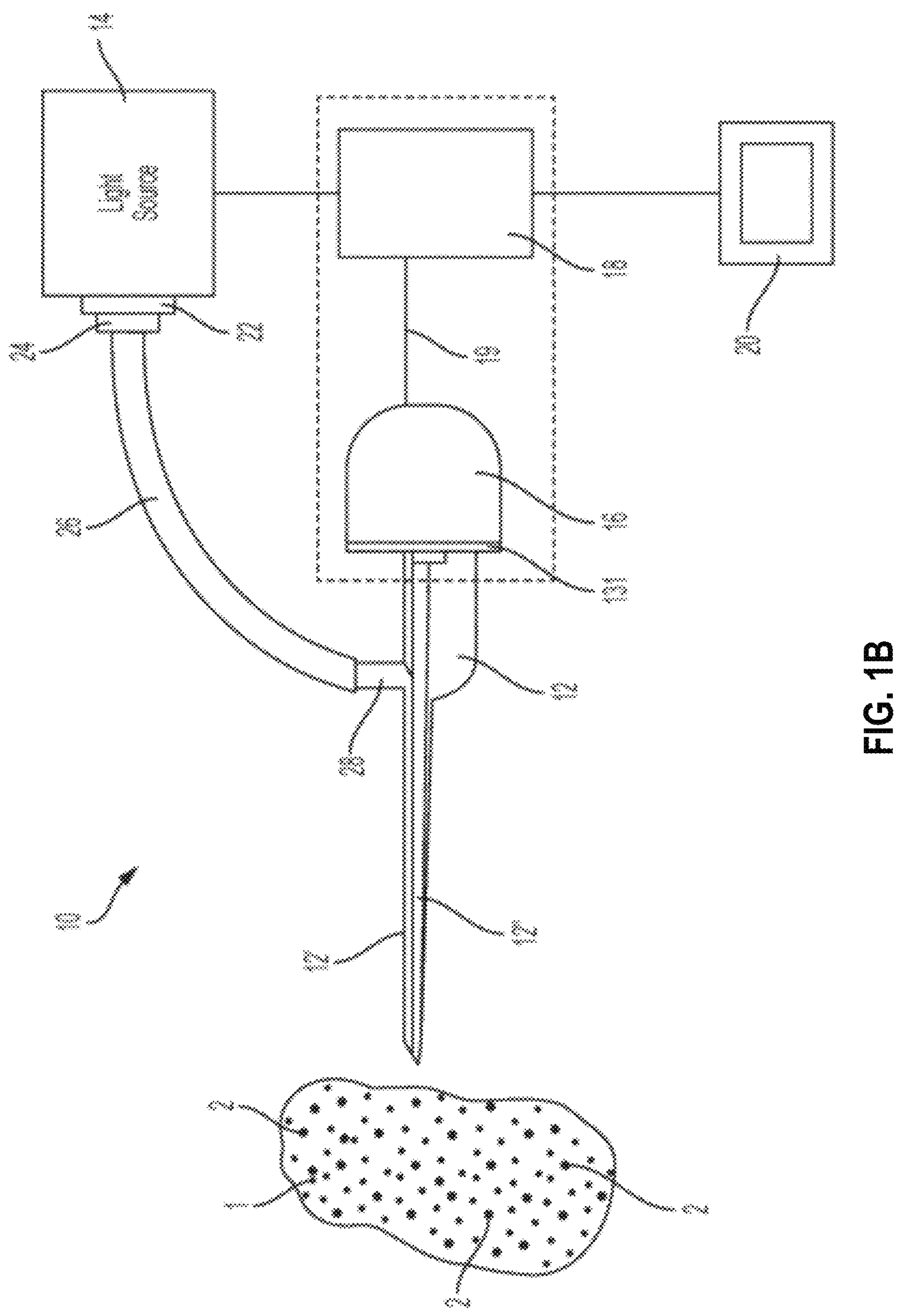
FIG. 1B is a diagram of a portion of the endoscopic camera system of FIG. 1A and a target object for imaging, according to some examples.

FIG. 1B shows an example of a portion of the endoscopic system 10 being used to illuminate and receive light from an object 1, such as a surgical site of a patient. The object 1 may include fluorescent markers 2, for example, as a result of the patient being administered a fluorescence imaging agent. The fluorescent markers 2 may comprise, for example, indocyanine green (ICG).

The light source 14 can generate visible illumination light (such as any combination of red, green, and blue light) for generating visible (e.g., white light) images of the target object 1 and, in some examples, can also produce fluorescence excitation illumination light for exciting the fluorescent markers 2 in the target object for generating fluorescence images. Illumination light is transmitted to and through an optic lens system 22 which focuses light onto a light pipe 24. The light pipe 24 may create a homogeneous light, which is then transmitted to the fiber optic light guide 26. The light guide 26 may include multiple optic fibers and is connected to a light post 28, which is part of the endoscope 12. The endoscope 12 includes an illumination pathway 12' and an optical channel pathway 12".

The endoscope 12 may include a notch filter 131 that allows some or all (preferably, at least 80%) of fluorescence emission light (e.g., in a wavelength range of 830 nm to 870 nm) emitted by fluorescence markers 2 in the target object 1 to pass therethrough and that allows some or all (preferably, at least 80%) of visible light (e.g., in the wavelength range of 400 nm to 700 nm), such as visible illumination light reflected by the target object 1, to pass therethrough, but that blocks substantially all of the fluorescence excitation light (e.g., infrared light having a wavelength of 808 nm) that is used to excite fluorescence emission from the fluorescent marker 2 in the target object 1. The notch filter 131 may have an optical density of OD5 or higher. In some examples, the notch filter 131 can be located in the coupler 13.

Figure 2:
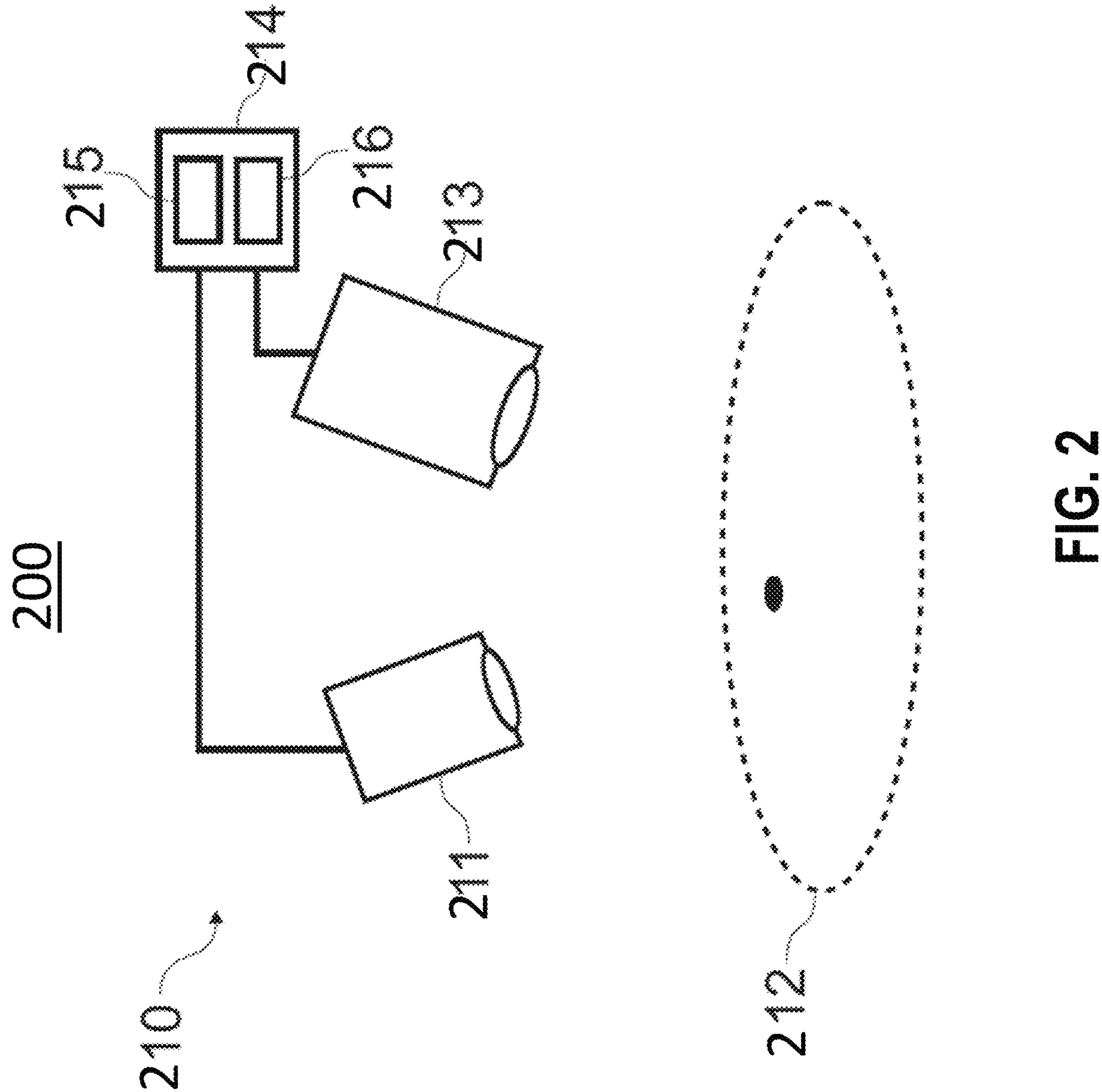
FIG. 2 illustrates a schematic view of a system for illumination and imaging according to some examples.

FIG. 2 illustrates an exemplary open field imaging system in accordance with some examples. FIG. 2 illustrates a schematic view of an illumination and imaging system 210 that can be used in open field surgical procedures. As may be seen therein, the system 210 may include an illumination module 211, an imaging module 213, and a video processor/illuminator (VPI) 214. The VPI 214 may include an illumination source 215 to provide illumination to the illumination module 211 and a processor assembly 216 to send control signals and to receive data about light detected by the imaging module 213 from a target 212 illuminated by light output by the illumination module 211. In one variation, the VPI 214 may comprise a separately housed illumination source 215 and the processor assembly 216. In one variation, the VPI 214 may comprise the processor assembly 216 while one or more illumination sources 215 are separately contained within the housing of the illumination module 211. The illumination source 215 may output light at different waveband regions, e.g., white (RGB) light, excitation light to induce fluorescence in the target 212, a combination thereof, and so forth, depending on characteristics to be examined and the material of the target 212. Light at different wavebands may be output by the illumination source 215 simultaneously, sequentially, or both. The illumination and imaging system 210 may be used, for example, to facilitate medical (e.g., surgical) decision making e.g., during a surgical procedure. The target 212 may be a topographically complex target, e.g., a biological material including tissue, an anatomical structure, other objects with contours and shapes resulting in shadowing when illuminated, and so forth. The VPI 214 may record, process, display, and so forth, the resulting images and associated information.

Figure 3:
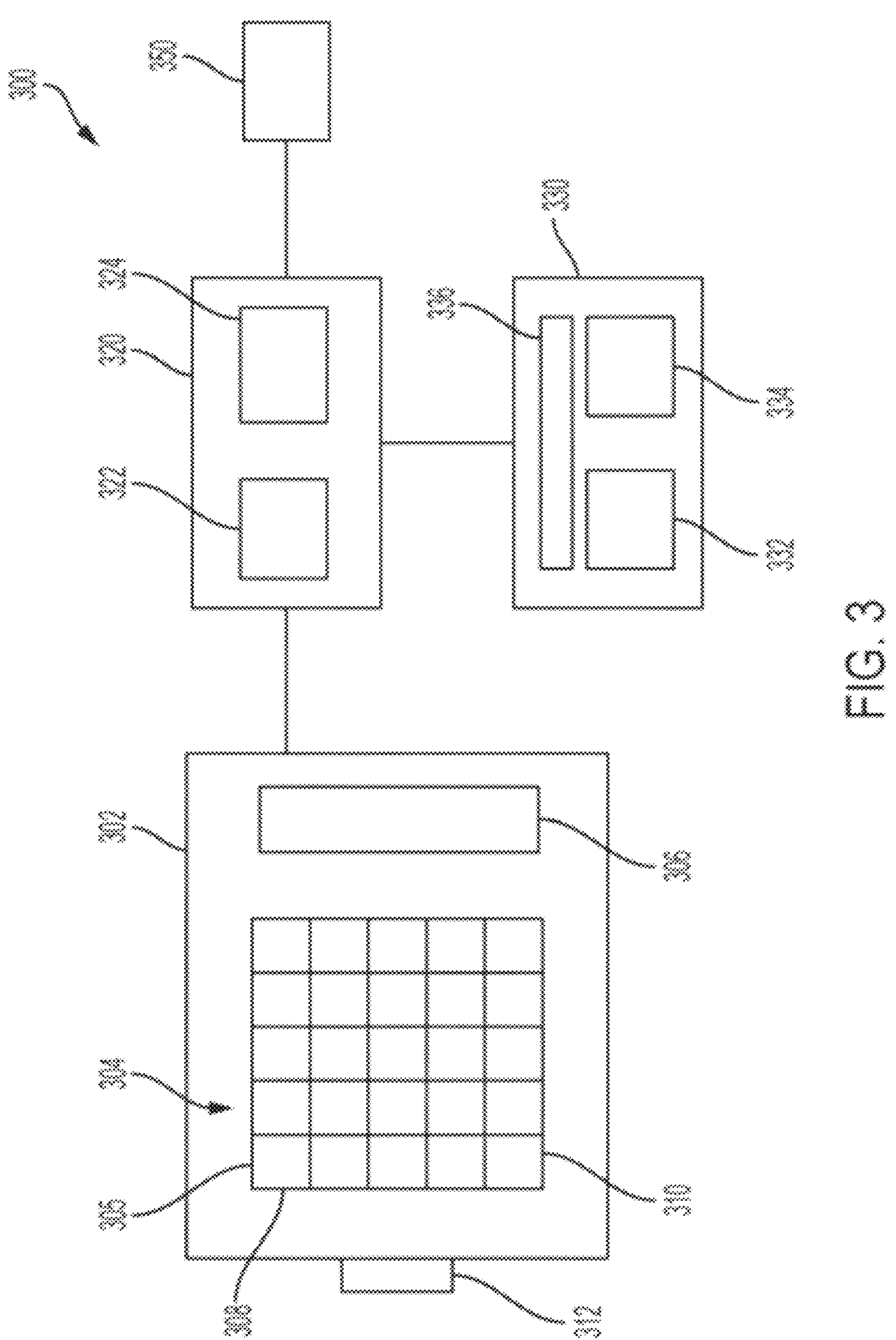
FIG. 3 is a block diagram of an imaging system, according to some examples.

FIG. 3 schematically illustrates an exemplary imaging system 300 that employs an electronic imager 302 to generate images (e.g., still and/or video) of a target object, such as a target tissue of a patient, according to some examples. The imager 302 may be a rolling shutter imager (e.g., CMOS sensors) or a global shutter imager (e.g., CCD sensors). System 300 may be used, for example, for the endoscopic imaging system 10 of FIG. 1A. The imager 302 includes a sensor 304 (for example, a CMOS sensor) having an array of pixels 305 arranged in rows of pixels 308 and columns of pixels 310. The imager 302 may include control components 306 that control the signals generated by the sensor 304. Examples of control components include gain circuitry for generating a multi-bit signal indicative of light incident on each pixel of the sensor 304, one or more analog-to-digital converters, one or more line drivers to act as a buffer and provide driving power for the sensor 304, row circuitry, and timing circuitry. A timing circuit may include components such as a bias circuit, a clock/timing generation circuit, and/or an oscillator. Row circuitry may enable one or more processing and/or operational tasks such as addressing rows of pixels 308, addressing columns of pixels 310, resetting charge on rows of pixels 308, enabling exposure of pixels 305, decoding signals, amplifying signals, analog-to-digital signal conversion, applying timing, read out and reset signals and other suitable processes or tasks. Imager 302 may also include a mechanical shutter 312 that may be used, for example, to control exposure of the sensor 304 and/or to control an amount of light received at the image sensor 304.

One or more control components may be integrated into the same integrated circuit in which the sensor 304 is integrated or may be discrete components. The imager 302 may be incorporated into an imaging head, such as camera head 16 of system 10.

One or more control components 306, such as row circuitry and a timing circuit, may be electrically connected to an imaging controller 320, such as CCU 18 of system 10. The imaging controller 320 may include one or more processors 322 and memory 324. The imaging controller 320 receives imager row readouts and may control readout timings and other imager operations, including mechanical shutter operation. The imaging controller 320 may generate image frames, such as video frames from the row and/or column readouts from the imager 302. Generated frames may be provided to a display 350 for display to a user, such as a surgeon.

The system 300 in this example includes a light source 330 for illuminating a target scene. The light source 330 is controlled by the imaging controller 320. The imaging controller 320 may determine the type of illumination provided by the light source 330 (e.g., white light, fluorescence excitation light, or both), the intensity of the illumination provided by the light source 330, and or the on/off times of illumination in synchronization with rolling shutter operation. The light source 330 may include a first light generator 332 for generating light in a first wavelength and a second light generator 334 for generating light in a second wavelength. In some examples, the first light generator 332 is a white light generator, which may be comprised of multiple discrete light generation components (e.g., multiple LEDs of different colors), and the second light generator 334 is a fluorescence excitation light generator, such as a laser diode.

The light source 330 includes a controller 336 for controlling light output of the light generators. The controller 336 may be configured to provide pulse width modulation of the light generators for modulating intensity of light provided by the light source 330, which can be used to manage over-exposure and under-exposure. In some examples, nominal current and/or voltage of each light generator remains constant and the light intensity is modulated by switching the light generators (e.g., LEDs) on and off according to a pulse width control signal. In some examples, a PWM control signal is provided by the imaging controller 336. This control signal can be a waveform that corresponds to the desired pulse width modulated operation of light generators.

The imaging controller 320 may be configured to determine the illumination intensity required of the light source 330 and may generate a PWM signal that is communicated to the light source 330. In some examples, depending on the amount of light received at the sensor 304 and the integration times, the light source may be pulsed at different rates to alter the intensity of illumination light at the target scene. The imaging controller 320 may determine a required illumination light intensity for a subsequent frame based on an amount of light received at the sensor 304 in a current frame and/or one or more previous frames. In some examples, the imaging controller 320 is capable of controlling pixel intensities via PWM of the light source 330 (to increase/decrease the amount of light at the pixels), via operation of the mechanical shutter 312 (to increase/decrease the amount of light at the pixels), and/or via changes in gain (to increase/decrease sensitivity of the pixels to received light). In some examples, the imaging controller 320 primarily uses PWM of the illumination source for controlling pixel intensities while holding the shutter open (or at least not operating the shutter) and maintaining gain levels. The controller 320 may operate the shutter 312 and/or modify the gain in the event that the light intensity is at a maximum or minimum and further adjustment is needed.

Clarifying and Enhancing Intraoperative Imaging Data

Figure 4:
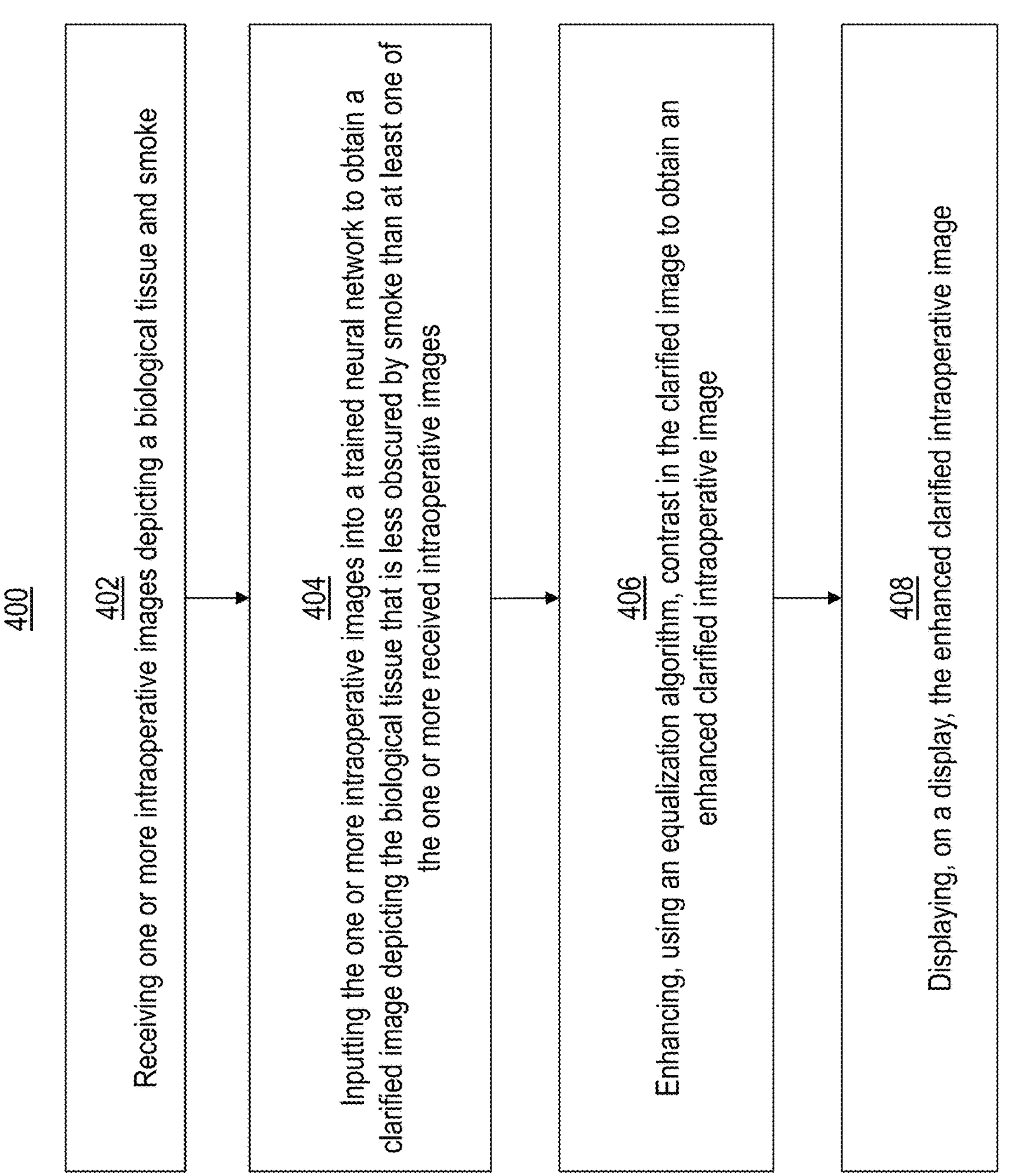
FIG. 4 illustrates an exemplary method for clarifying and enhancing intraoperative images, according to some examples.

FIG. 4 illustrates an exemplary method 400 for clarifying and enhancing intraoperative images, according to some examples. Method 400 is performed, for example, using one or more electronic devices implementing a software platform. In some examples, method 400 is performed using a client-server system, and the blocks of method 400 are divided up in any manner between the server and one or more client devices. In some examples, method 400 is performed using only a client device or only multiple client devices. In method 400, some blocks are, optionally, combined, the order of some blocks is, optionally, changed, and some blocks are, optionally, omitted. In some examples, additional steps may be performed in combination with the method 400. Accordingly, the operations as illustrated (and described in greater detail below) are exemplary by nature and, as such, should not be viewed as limiting.

At block 402, an exemplary system (e.g., one or more electronic devices) receives one or more intraoperative images depicting a biological tissue and smoke. In some examples, the one or more intraoperative images can be captured during an operation such as an endoscopic imaging procedure or open field surgical imaging procedure. Although the intraoperative image may be captured during an endoscopic procedure, the method 400 may exclude an invasive surgical step. For instance, the method 400 may exclude insertion of an endoscopic imager into a lumen in the body. The endoscopic imager may be pre-inserted into a lumen in the body. The one or more images can be part of an intraoperative video stream depicting the surgical site. In some examples, a plurality of intraoperative images are received, which can provide additional image data and temporal information that may improve the clarifying and enhancing performance of method 400. The one or more images can be white light images, in some examples.

In some examples, the biological tissue is not visible or has reduced visibility in the intraoperative image because it is covered or obscured by smoke. The smoke may be generated because tissues may be burnt or cauterized during surgical procedures. The smoke is captured by the camera and can reduce the visibility of the biological tissue.

Figure 5:
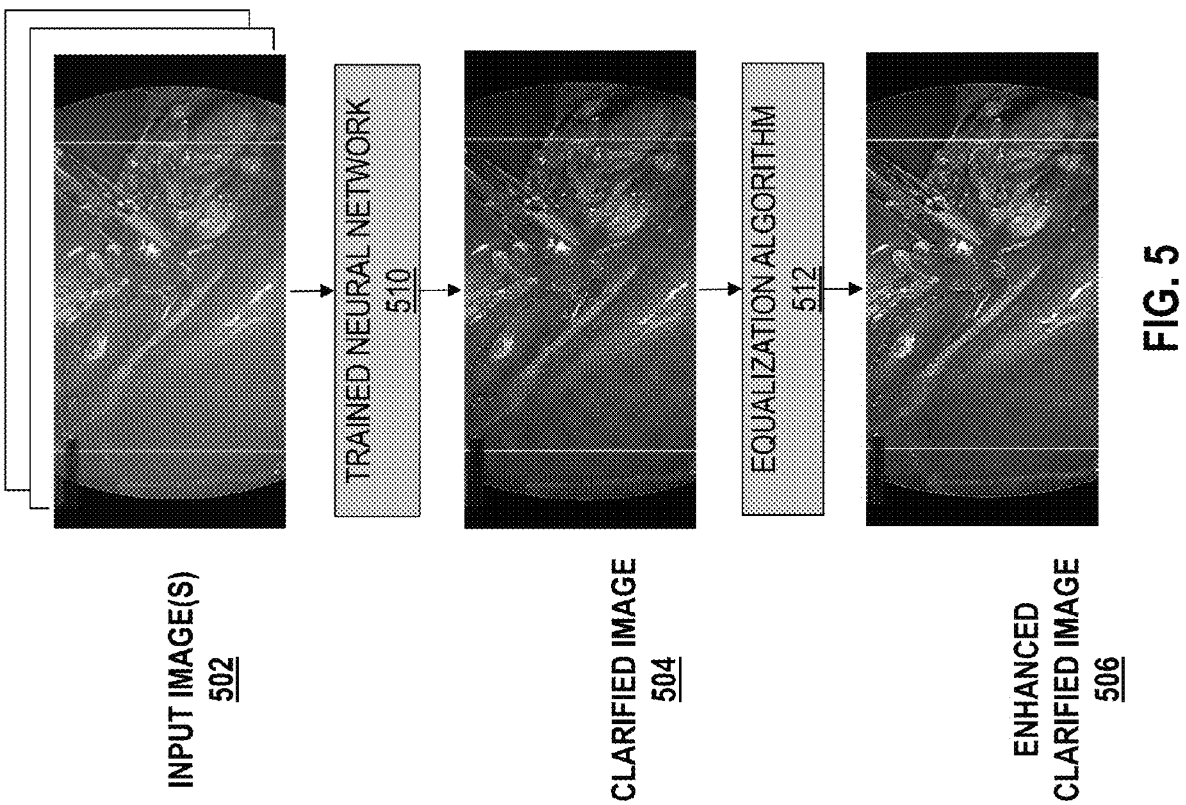
FIG. 5 illustrates an exemplary workflow for clarifying and enhancing an intraoperative image, according to some examples.

As an example, FIG. 5 illustrates an exemplary workflow for clarifying and enhancing an intraoperative image, according to some examples. As shown, one or more input images 502 include an intraoperative image depicting biological tissues at a surgical site. In the input images 502, smoke reduces visibility of the surgical site, making it more difficult for surgeons to rely on the image to carry out the procedure.

In some examples, the system analyzes the received one or more intraoperative images to detect smoke in at least one of the one or more images. In accordance with a determination that smoke is detected in the one or more images (e.g., smoke level exceeds a predefined threshold), the system proceeds to blocks 404 and 406 to clarify and enhance a smoky image of the one or more images before displaying the image on a display. In accordance with a determination that smoke is not detected in the one or more images (e.g., smoke level does not exceed the predefined threshold), the system foregoes blocks 404 and 406 and displays the one or more images at block 408, for example, as part of an intraoperative video stream.

Optionally, one or more conditions for proceeding to blocks 404 and 406 may be applied in addition to or alternatively to the determination that smoke is detected in the one or more images as described above. For example, the system may proceed to blocks 404 and 406 in accordance with a determination that a surgical context indicates that smoke is likely to appear. More specifically, the system may proceed to blocks 404 and 406 in accordance with a determination that the surgery has reached a certain phase (e.g., a phase in which electrocauterization is likely to occur), for example by automatically detecting surgical phases. Optionally, the system may proceed to blocks 404 and 406 in accordance with a determination that one or more instruments appear in a field of view, for example leveraging automatic tool detection to determine when tools likely to create surgical smoke are present.

Optionally, one or more of the above-specified conditions (or other conditions) may be applied to determine whether to apply a smoke detection algorithm to determine whether smoke is present in an image. That is, one or more of the above-specified conditions (or other conditions) may be applied as an initial determination, and a smoke-detection algorithm may then be applied as an optional subsequent determination. Optionally, then only in accordance with both the initial and subsequent determination satisfying predetermined criteria may the system proceed to blocks 404 and 406.

Applying one or more additional conditions such as these to determine whether to enhance an image and/or whether to apply a smoke detection algorithm (e.g., to thereby determine whether to subsequently enhance an image) may improve system efficiency. While applying one or more surgical phase detection algorithms and/or object detection algorithms (e.g., tool detection algorithms) may require the use of processing resources and may introduce time delays, applying these algorithms may also afford advantages such as improving efficiencies regarding when smoke-detection algorithms and/or image enhancement algorithms are applied. In systems in which one or more surgical phase detection algorithms and/or object detection algorithms are applied for one or more additional purposes (aside from triggering image enhancement and/or smoke detection algorithms), the efficiencies introduced by making image enhancement and/or smoke-detection contingent on the outcomes of said surgical phase detection algorithms and/or object detection algorithms may be achieved without significant tradeoff.

At block 404, the system inputs the one or more intraoperative images into a trained neural network to obtain a clarified image depicting the biological tissue that is less obscured by smoke than at least one of the received one or more intraoperative images. In the example depicted in FIG. 5, the system inputs the one or more input images 502 (e.g., intraoperative images) into a trained neural network 510. The trained neural network 510 outputs a clarified image 504. As shown, the clarified image 504 depicts biological tissues that are less obscured by smoke than the smoky image(s) of the one or more input images 502. The neural network comprises a collection of connected nodes (as known as artificial neurons). In some examples, the trained neural network is a trained convolutional neural network ("CNN"), as described in more detail with reference to FIG. 7, although other neural network types may be used (e.g., a recurrent neural network (RNN), a generative adversarial network (GAN), or a temporal convolutional network (TCN)).

In some examples, the system analyzes the received one or more intraoperative images to determine a smoke level in the received one or more intraoperative images, and selects the trained neural network based on the determined smoke level. For example, the system can maintain multiple trained neural networks configured to process images of different smoke levels. For example, the system can maintain a first trained neural network configured to process images of a first smoke level (e.g., low) and a second trained neural network configured to process images of a second smoke level different from the first smoke level (e.g., high). Accordingly, the system can select a neural network that is best suited for processing the one or more intraoperative images given the smoke level. These neural networks can be trained using different training images corresponding to different smoke levels. For example, the first trained neural network can be trained using images of the first smoke level, while the second trained neural network can be trained using images of the second smoke level, such that performance of each neural network is optimized for a specific smoke level.

At block 406, the system enhances, using an equalization algorithm, contrast in the clarified image to obtain an enhanced clarified intraoperative image. In the example depicted in FIG. 5, the clarified image 504 is enhanced by an equalization algorithm 512 to obtain enhanced and clarified image 506. As shown, the enhanced and clarified image 506 is more sharpened and provides improved visibility than the clarified image 504.

The equalization algorithm improves the local contrast and enhances the definitions of edges in various regions of the image. In some examples, the equalization algorithm is configured to enhance the contrast in the clarified image without amplifying noise in the image. In some examples, the equalization algorithm is the Adaptive Histogram Equalization (AHE) algorithm. In some examples, the equalization algorithm is the Contrast Limited Adaptive Histogram Equalization (CLAHE) algorithm.

Figure 6:
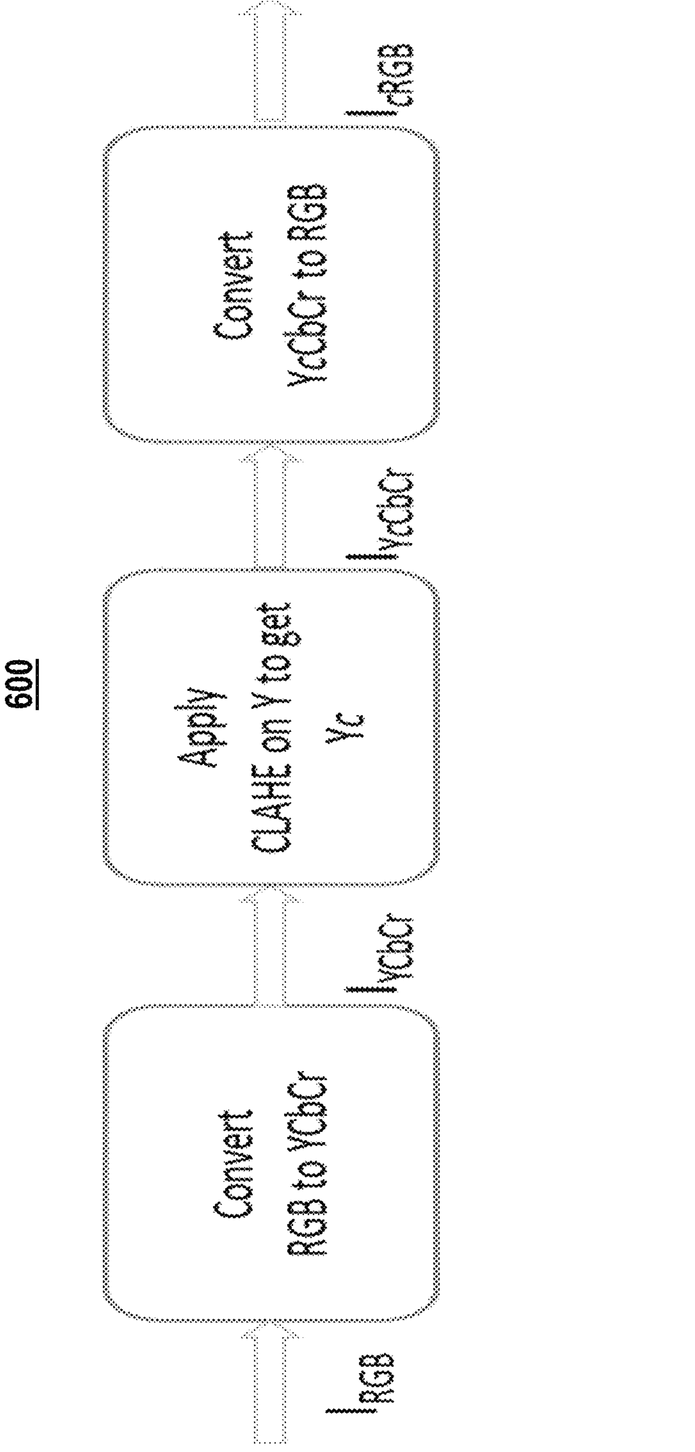
FIG. 6 illustrates an exemplary process for applying CLAHE to enhance an image, in accordance with some examples.

FIG. 6 illustrates an exemplary process 600 for applying CLAHE to enhance an image, in accordance with some examples. With reference to FIG. 6, the system can receive an input image IRGB, which can be a clarified image obtained in block 404. The system converts the image IRGB from a RGB color format to a YCbCr color format to obtain $I_{YCbCr}$. The system then applies the CLAHE algorithm to the Y component of $I_{YCbCr}$. The system then converts $I_{YCbCr}$ from the YCbCr format to the RGB color format to obtain the enhanced image $I_{cRGB}$.

In CLAHE, each image is divided into predefined grids or blocks. In each local grid, histogram is computed. From that, probability density function (PDF) and cumulative distribution function (CDF) are estimated. For each local PDF, if a particular gray level frequency is above a predefined clip limit set, extra contribution can be redistributed equally among all other gray levels. However, this process may cause some gray levels to have contribution higher than predefined clip limit. To avoid the issue, the redistribution can be repeated. In each grid, the system can recalculate local CDFs with modified PDFs and perform histogram equalization (HE). In HE, transformation function (recalculated CDF) is applied on original pixel intensities.

In some examples, when applying the CLAHE algorithm, each pixel is transformed based on the histogram of a square or grid surrounding the pixel. Further, the contrast amplification in the vicinity of a given pixel value is given by the slope of the transformation function. This is proportional to the slope of the neighborhood cumulative distribution function (CDF) and therefore to the value of the histogram at that pixel value. CLAHE limits the amplification of noise by clipping the histogram at a predefined value before computing the CDF. This limits the slope of the CDF and therefore of the transformation function. The value at which the histogram is clipped, the so-called clip limit, depends on the normalization of the histogram and thereby on the size of the neighborhood region. In some examples, the Y component of $I_{YCbCr}$ is enhanced with CLAHE with the clip limit of 0.75 and grid size of (8,8). In some examples, the CLAHE algorithm is applied based on parameters optimized for endoscopic images. For example, the clip limit and the tile grid size are tuned to obtain the optimal setting (e.g., using local heuristics).

Turning back to FIG. 4, at block 408, the system displays, on a display, the enhanced clarified intraoperative image. In some examples, the system displays the enhanced clarified intraoperative image as part of an intraoperative video stream (e.g., a real-time video stream) to aid the surgical procedure.

In some examples, the intraoperative image is captured during a surgical procedure, and the system can provide a recommendation related to the surgical procedure based on the enhanced clarified intraoperative image. The recommendation can be related to navigating a surgical instrument. The recommendation can be an indication of an anatomical structure to operate on or to avoid. The recommendation can be related to administration of a particular treatment. The recommendation can be related to identification of a high-risk area or a potential complication. In some examples, the recommendation is provided during the surgery such that the surgeon can alter the course of action in real time.

In some examples, the enhanced clarified image can be provided (e.g., displayed) to a medical practitioner, who can review the image to identify, recommend, and/or administer a treatment or some other course of action to the patient pre-surgery, during surgery, or post-operatively. In some examples, the enhanced clarified image can be provided to a computer-based system, which processes the image to identify, recommend, and/or administer a treatment or some other course of action to the patient. For example, the system can provide the enhanced clarified image to a classification model to automatically identify one or more complications. Based on the identified issue, a treatment or some other course of action can be automatically recommended (e.g., via one or more graphical user interfaces). The treatment can also be automatically administered, for example, by a medical device (e.g., a surgical robot) based on the automatically recommended treatment.

Figure 7:
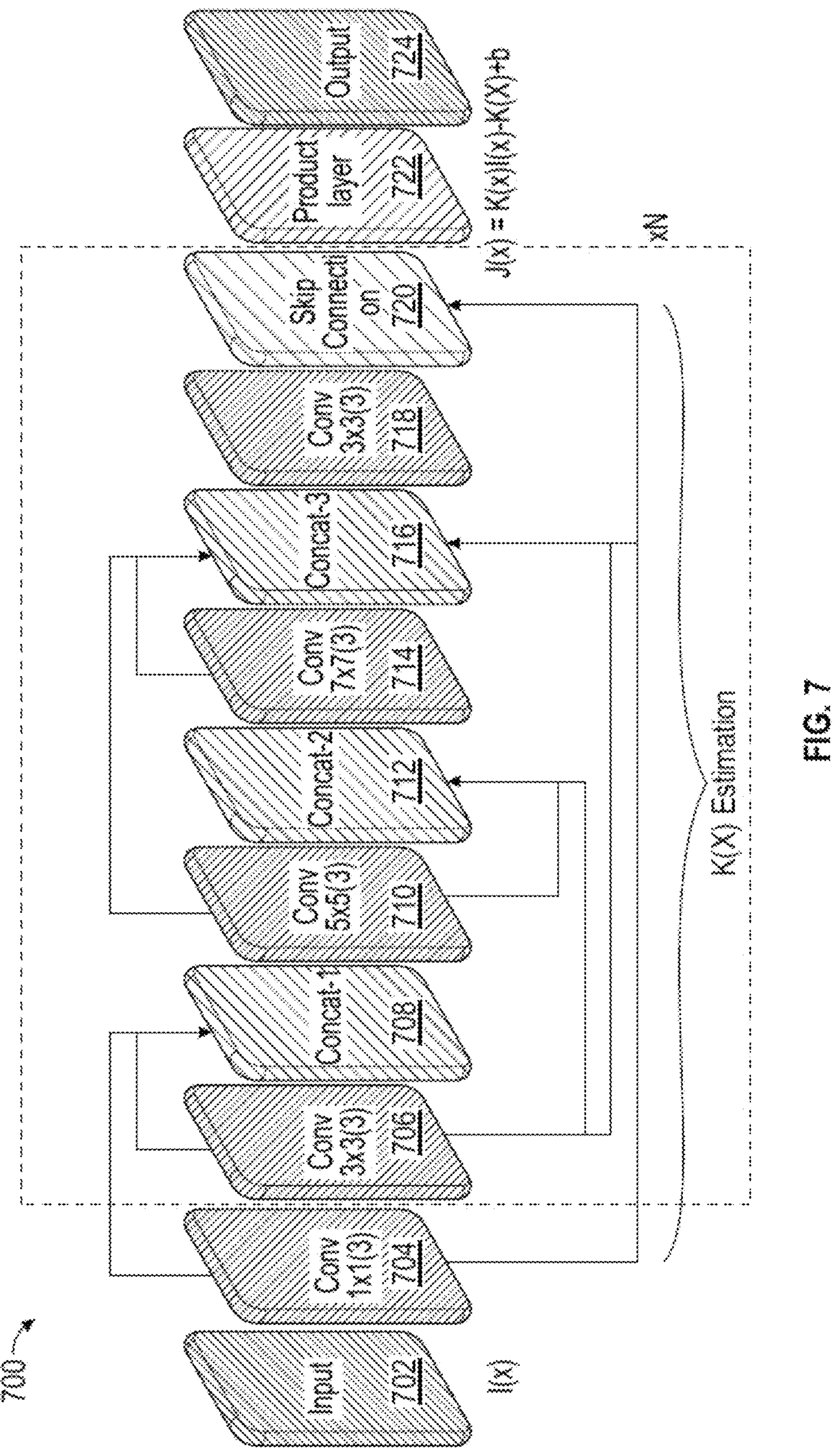
FIG. 7 illustrates an exemplary neural network configured to receive an input image and output a clarified image, in accordance with some examples.

FIG. 7 illustrates an exemplary neural network 700 configured to receive an input image 702 and output a clarified image 724, in accordance with some examples. The neural network 700 can be the trained neural network used in block 404 in FIG. 4 and/or the trained neural network 510 in FIG. 5. In the depicted example, the neural network 700 is a convolutional neural network ("CNN"). A CNN comprises a plurality of layers and one or more layers of the plurality of layers are configured to perform convolutions, as described below. In order to obtain the clarified output image, the CNN can be configured to optimize a transmission map and an atmospheric light in an atmospheric scattering equation, as described below.

Figure 8:
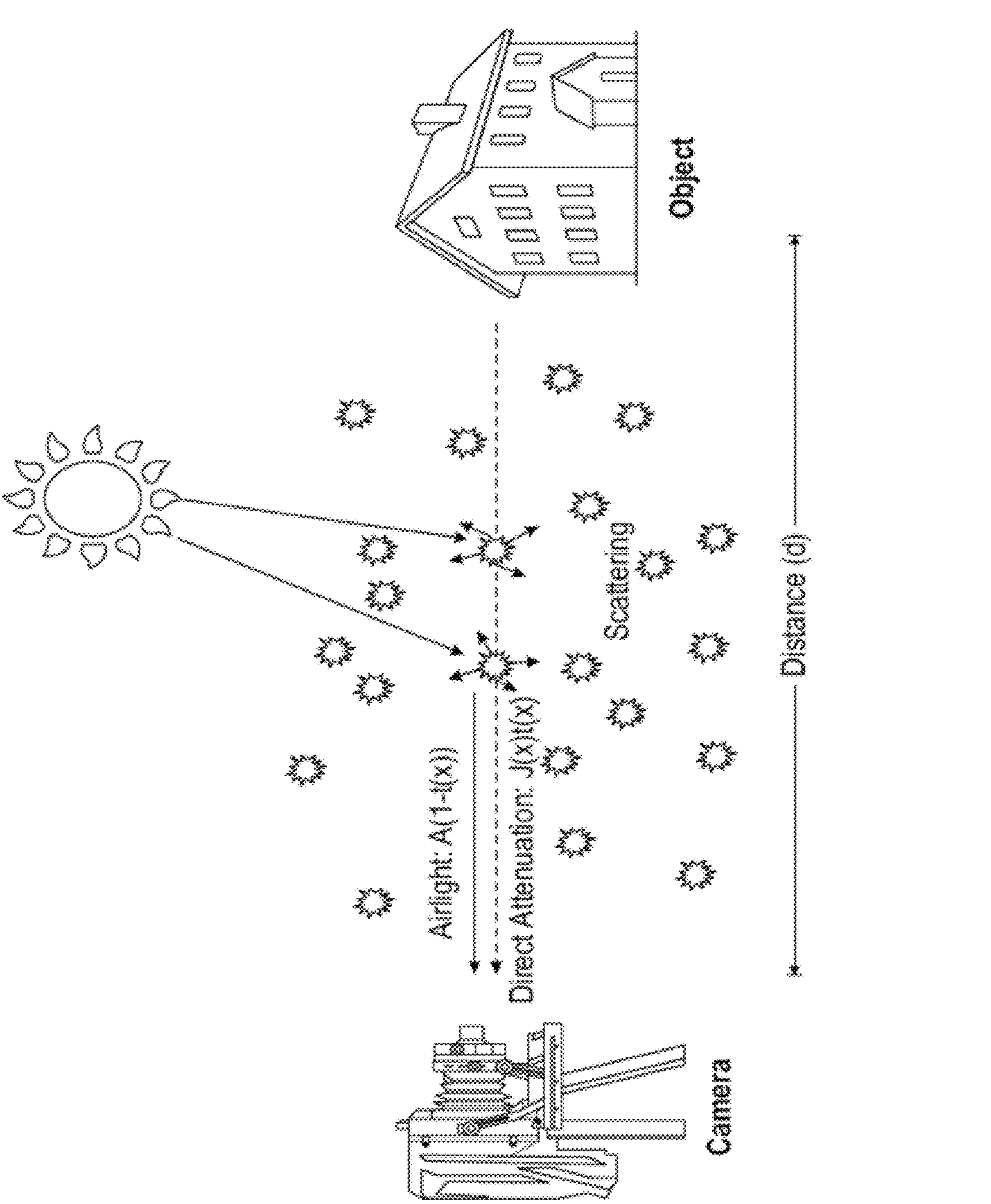
FIG. 8 illustrates parameters of an exemplary atmospheric scattering equation, in accordance with some examples.

Specifically, the input image 702, or I(x), is a smoky image (i.e., an image depicting smoke) and can be represented by the atmospheric scattering equation below (also illustrated in FIG. 8):

$$I(x)=J(x)t(x)+A(1-t(x))$$

Where:

A: Atmospheric Light t(x): Transmission Map

J(x): Haze-Free/Smoke-Free Image

Accordingly, the clarified image J(x) can be derived as follows:

$$J(x)=K(x)I(x)-K(x)+b$$

Where:

$$K(x)=\frac{\frac{1}{t(x)}(I(x)-A)+(A-b)}{I(x)-1}$$

b: Bias

K(x): Joint parameter for estimating A and t(x)

As shown above, the original atmospheric scattering equation is modified such that the system needs to only estimate one joint parameter K(x), rather than estimating the atmospheric light A and the transmission map t(x) separately. In other words, the modified scattering equation is formulated in such a way that it jointly finds the atmospheric light and transmission map value by minimizing the overall loss of a neural network, instead of optimizing them individually.

The neural network 700 is configured to estimate the joint parameter K(x) using a set of convolution, concatenation and skip connection layers. With reference to FIG. 7, the neural network 700 comprises convolution layers (e.g., 704, 706) followed by concatenation layers (708, 712, 716) along with skip connections (e.g., 720) to bypass gradient to initial layers. In the depicted example, convolutional layer 704 comprises a filter (also known as a kernel) of size 1×1 and three filters. The convolutional layer applies a convolution operation to the input using the filters. Specifically, the convolution involves multiplying pixel values by weights represented in the filter and summing them. The final output of the convolutional layer is a vector provided to the next layer. Similarly, convolutional layer 706 comprises a filter of size 3×3 and three filters; convolutional layer 710 comprises a filter of size 5×5 and three filters; convolutional layer 714 comprises a filter of size 7×7 and three filters; convolutional layer 718 comprises a filter of size 3×3 and three filters. Layers 704-720 are configured to estimate K(x). Further, the layers 706-720 are stacked N times to refine estimation and thereby facilitate efficient smoke removal.

After the neural network 700 obtains K(x), the clarified image 724 can be obtained using the product layer 722 according to:

$$J(x)=K(x)I(x)-K(x)+b$$

Figure 9:
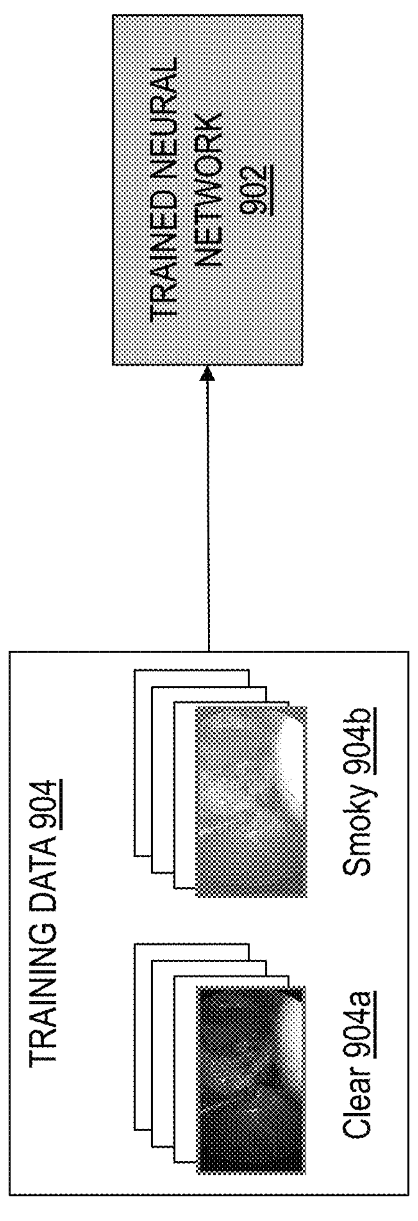
FIG. 9 illustrates an exemplary process for training a neural network configured to receive an input image (e.g., a smoky image) and output a clarified image, in accordance with some examples.

FIG. 9 illustrates an exemplary process for training a neural network configured to receive an input image (e.g., a smoky image) and output a clarified image, in accordance with some examples. The neural network 902 can be the neural network used in block 404 in FIG. 4, the neural network 510 in FIG. 5, and/or the neural network 700 in FIG. 7. With reference to FIG. 9, the neural network 902 is trained using training data 904. The training data 904 comprises a plurality of smoke-free training images 904*a* and a plurality of smoky training images 904*b*. In some examples, the smoke-free training images 904*a* can be selected from surgical endoscopic videos with no smoke present. In some examples, the smoky training images 904*b* are simulated images that are generated using the smoke-free training images 904*a*, as described below.

Figure 10:
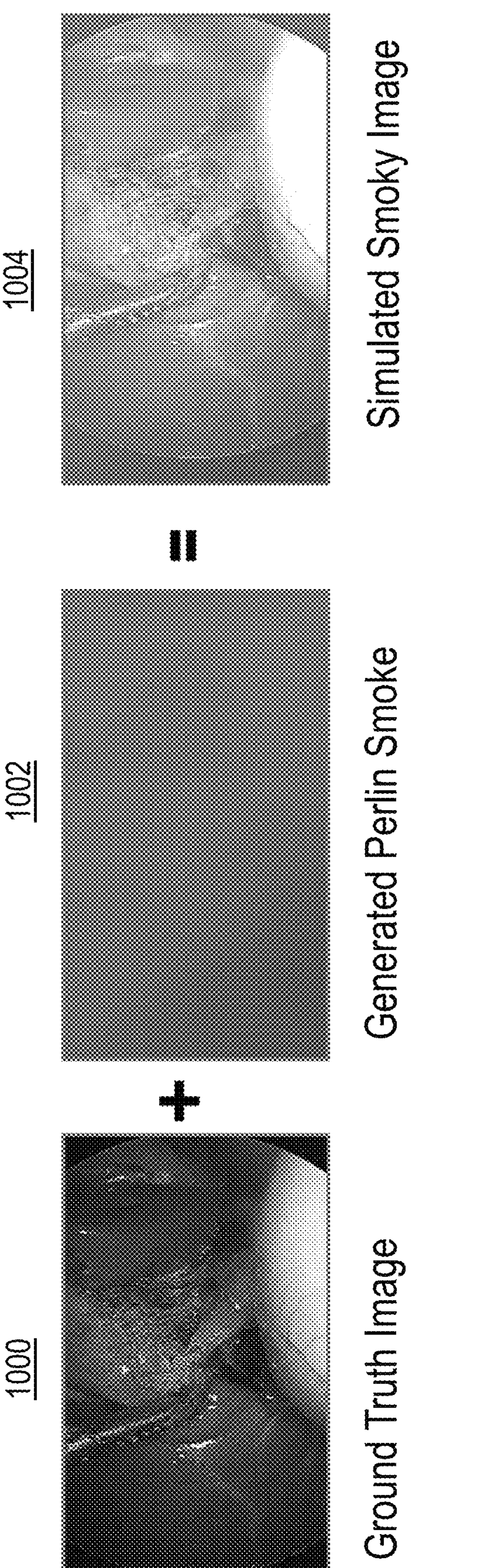
FIG. 10 illustrates an exemplary process for generating a simulated smoky image based on a smoke-free image, in accordance with some examples.

FIG. 10 illustrates an exemplary process for generating a simulated smoky image based on a smoke-free image, in accordance with some examples. As shown, the system receives a smoke-free image 1000 (e.g., one of the smoke-free training images 904*a*). The system further generates a simulated smoke layer 1002. In some examples, the simulated smoke layer 1002 is generated using Perlin noise using one or more noise parameters, although it should be appreciated that other synthetic noise (e.g., other types of gradient noise or any type of software-generated smoke such as Blender smoke) can be used to generate the simulated smoke layer. The system then aggregates the smoke-free image 1000 and the simulated smoke layer 1002 to obtain the simulated smoky image 1004. In some examples, aggregating the smoke-free image 1000 and the simulated smoke layer 1002 comprises superposing the simulated smoke layer 1002 onto the smoke-free image. Optionally, aggregating the smoke-free image 1000 and the simulated smoke layer 1002 comprises performing a pixel-wise weighted addition.

The smoke-free image 1000 and/or the simulated smoke layer 1002 may be weighted before the aggregation. For example, the system can apply a first weight to the smoke-free image 1000 and a second weight to the simulated smoke layer 1002 and then perform a pixel-wise aggregation of the two weighted images. As another example, a weight is only applied to the simulated smoke layer 1002. The first and/or the second weights can be selected to control the level of smoke in the resulting image. The higher the second weight compared to the first weight, the more smoky the resulting image will be. The resulting smoky image 1004 can form an image pair with the smoke-free image 1000 and be used to train the neural network. In some examples, the system can generate smoky images having different smoke levels (e.g., low, medium, and high). The different smoke levels can be defined using different ranges of weights. As described above, the neural network can be trained using smoky training images of different smoke levels such that it can clarify any image regardless of its smoke levels. Alternatively, a separate neural network is trained using smoky training images of a specific smoke level.

While physical models such as atmospheric scattering models may be utilized to model smoke parameters efficiently, such models may still be limited by relying on generated smoke. It may be the case that such artificially generated smoke cannot be distributed uniformly and thus cannot be simply computed by a scattering model. An alternative approach is to use paired image-to-image translation GANs. These algorithms require corresponding sets of images with and without ground-truth smoky conditions during training, and thus also rely on synthetically generated smoke data.

To address these limitations, a method for desmoking laparoscopic videos may be based on cycle-consistency GAN (CycleGAN), using two novel loss functions (inter-channel discrepancies and dark channel prior). This architecture can be trained on unpaired images (clear versus smoky). Such an algorithm and associated training dataset (containing real smoky laparoscopic images) may be adapted to implement an alternative realization of the techniques disclosed herein. Namely, such a training dataset (or any other dataset containing real smoky laparoscopic images) may be used as a training seed for a generative model such as a conditional GAN or an unconditional GAN (such as StyleGAN2). A generative model (such as an unconditional GAN such as StyleGAN2) trained on such data (real smoky laparoscopic images) may allow generating an unlimited number of realistic-looking artificial images, both clear and smoky. Those artificial images can then be used to train any image-to-image translation algorithm that does not rely on paired images (e.g., DeSmoke-LAP).

An advantage of this approach is that it may allow creation of as large a training dataset as needed without relying on the expensive and time-consuming process of data collection and pre-processing (e.g., anonymization, manual smoky frames extraction). These large datasets can then be used effectively for subsequent training tasks, for example for training image-to-image translation algorithms or other algorithms that convert smoky images to corresponding clear images.

Figure 11A:
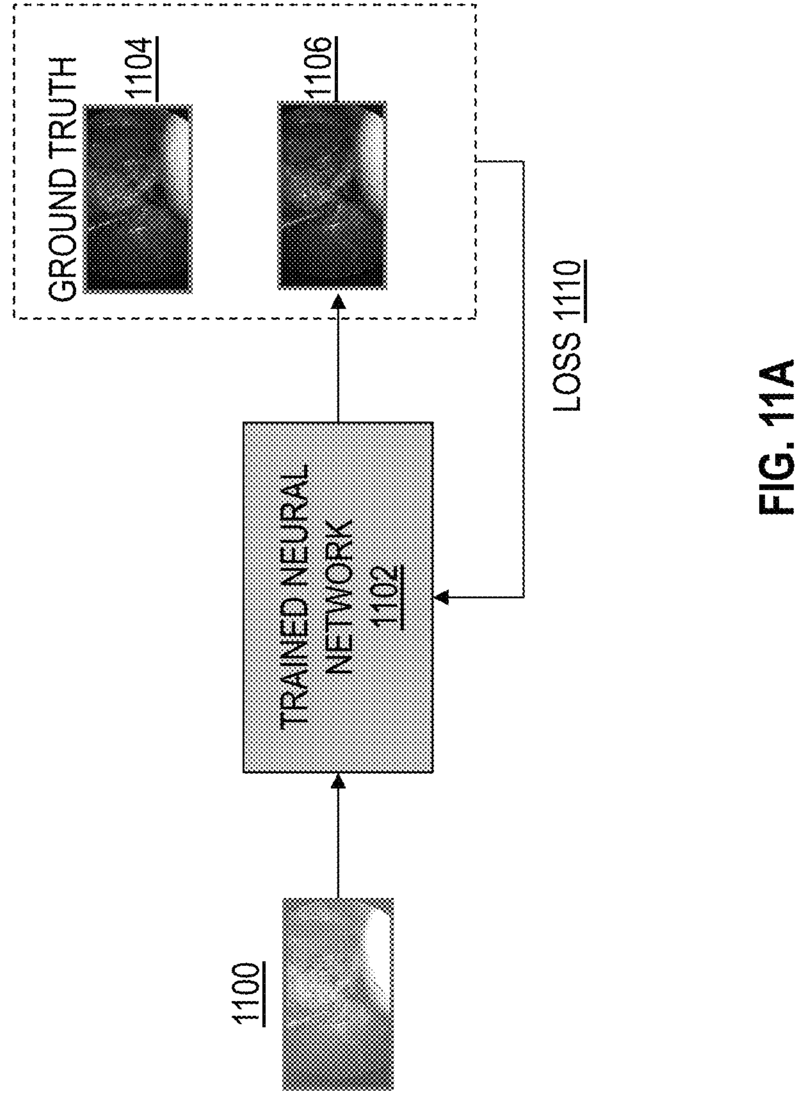
FIG. 11A illustrates an exemplary process for training the neural network without taking into account the downstream CLAHE algorithm, in accordance with some examples.
Figure 11B:
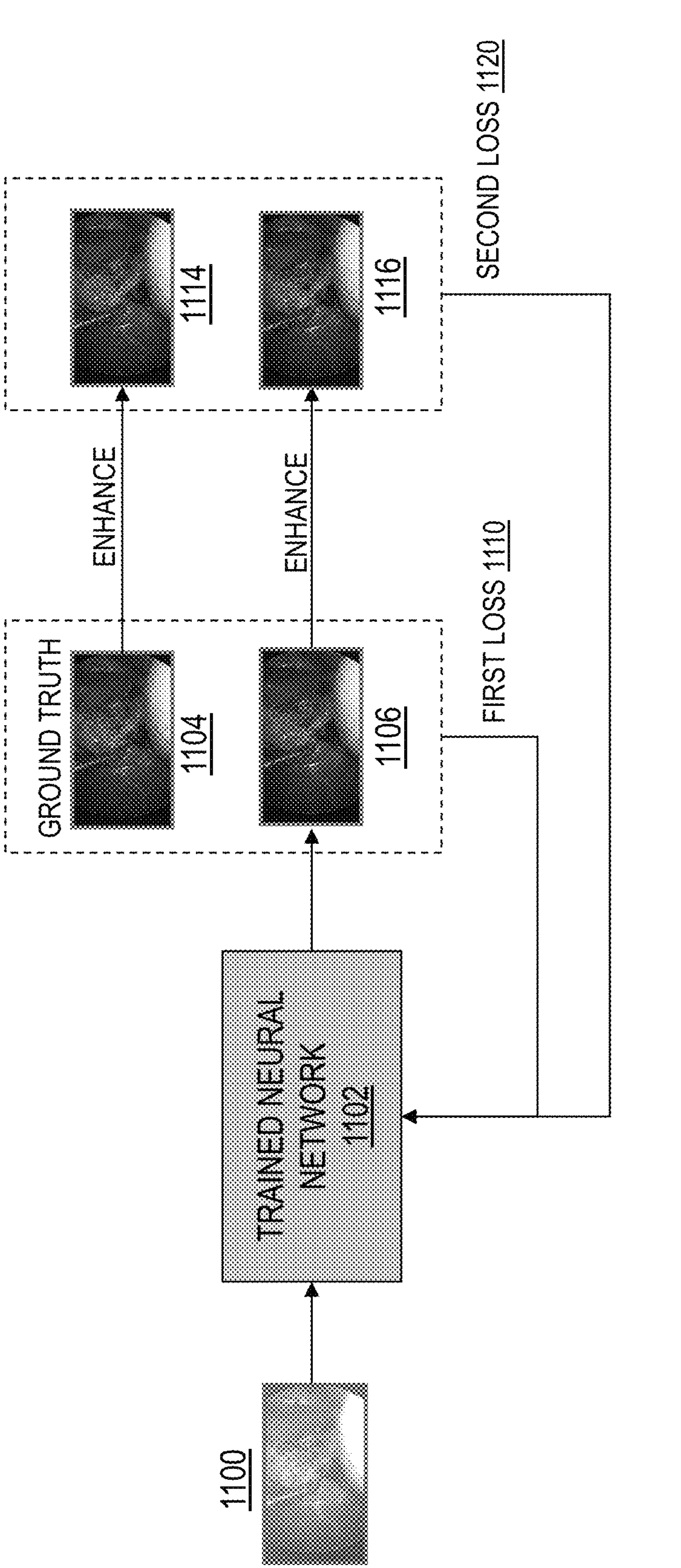
FIG. 11B illustrates an exemplary process for training the neural network while taking into account the downstream CLAHE algorithm, in accordance with some examples.

FIGS. 11A and 11B illustrate exemplary processes for training a neural network for clarifying images, in accordance with some examples. In particular, FIG. 11A illustrates an exemplary process for training the neural network without taking into account the downstream CLAHE algorithm, while FIG. 11B illustrates an exemplary process for training the neural network while taking into account the downstream CLAHE algorithm.

With reference to FIG. 11A, during training, the system receives a smoky training image 1100 (e.g., from images 904*b* in FIG. 9) and receives a smoke-free training image 1104 (e.g., from images 904*a* in FIG. 9). The smoky training image 1100 is inputted into the neural network 1102 to obtain a generated image 1106. The system then compares the generated image 1106 with the smoke-free training image 1104 and calculating a loss 1110 (e.g., mean squared error) based on the comparison. The system then updates the neural network (e.g., by updating the weights of the neural network) based on the loss 1110.

With reference to FIG. 11B, during training, the system receives a smoky training image 1100 and receives a smoke-free training image 1104 corresponding to the simulated smoky training image. The system inputs the smoky training image 1100 into the neural network 1102 to obtain a generated image 1106, and calculates a first loss 1110 (e.g., mean squared error) based on the generated image 1106 and the smoke-free training image 1104. The system enhances the smoke-free training image 1104 using an equalization algorithm (e.g., CLAHE) to obtain an enhanced smoke-free training image 1114. The system further enhances the generated image 1106 using the equalization algorithm to obtain an enhanced generated image 1116. The system then calculates a second loss 1120 based on the enhanced smoke-free training image 1114 and the enhanced generated image 1116. In some examples, the second loss is calculated as the structural similarity index (SSIM) loss. The system then updates the neural network based on the first loss 1110 and the second loss 1120. Accordingly, the system is trained to produce an image that is well-suited for downstream enhancement (e.g., downstream CLAHE).

During the training processes in FIGS. 11A and 11B, the system can tune various hyperparameters of the neural network (e.g., layers and filters of the neural network). In some examples, grid search is used to select the optimal hyperparameters. In some examples, the system can vary learning rates and epochs during the training process.

After training, the trained neural network can be tested. In some examples, the trained neural network is tested using simulated data. For example, a simulated smoky image can be inputted into the neural network to obtain a clarified image, which in turn is compared against the ground-truth image (i.e., the smoke-free image from which the simulated smoky image is generated) to determine the effectiveness of smoke removal by the neural network (e.g., based on mean squared error, structural similarity index, etc.). In some examples, the network can tested using real, non-simulated smoky images. The clarified images can be analyzed (e.g., by a subject matter expert) to determine the effectiveness of smoke removal.

Figure 12:
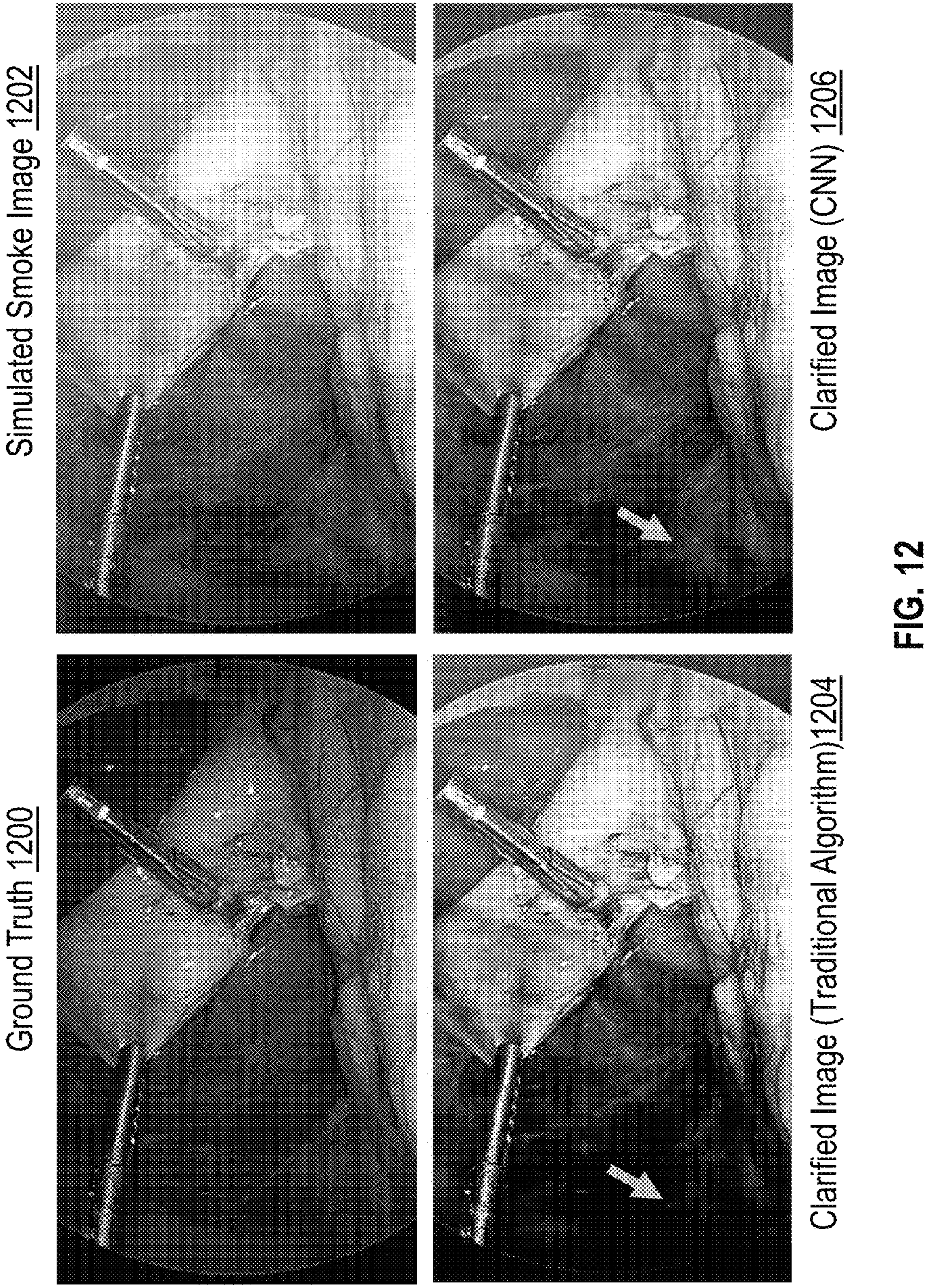
FIG. 12 illustrates a comparison of exemplary images, in accordance with some examples.

FIG. 12 illustrates a comparison of exemplary images, in accordance with some examples. Image 1200 is a smoke-free image of biological tissues. Image 1202 is a simulated smoky image generated based on image 1200 using techniques described with reference to FIG. 10. The smoky image 1202 is inputted into a traditional de-smoking algorithm to obtain image 1204. The smoky image 1202 is also inputted into a trained CNN as described herein to obtain image 1206. As shown, the CNN provides a better result than the traditional de-smoking algorithm as the CNN effectively removes smoke while providing more details in low-contrast regions, as indicated by the arrows.

Figure 13:
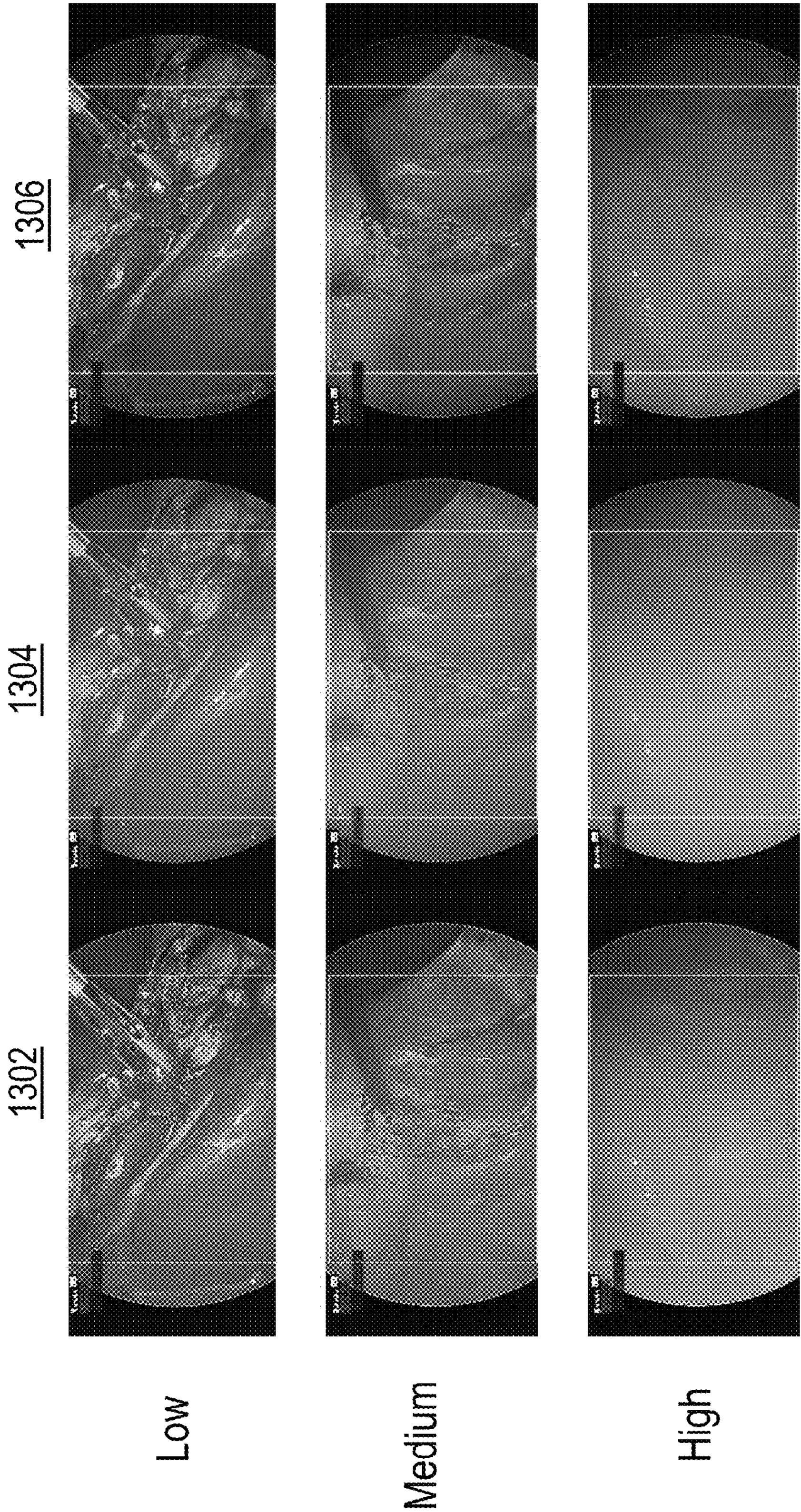
FIG. 13 illustrates a comparison of exemplary images, in accordance with some examples.

FIG. 13 illustrates a comparison of exemplary images, in accordance with some examples. Three input images 1302 having varying smoking levels are provided to a traditional de-smoking algorithms to obtain clarified images 1304. The three input images 1302 are also provided to a trained CNN as described herein to obtain clarified images 1306. As shown, the CNN provides better performance as it is more effective at removing smoke, enhancing structural fidelity, and preserving more color across all three images. With the traditional algorithm, the color saturates to grey scale. The images 1306 can be further enhanced using CLAHE to improve contrast, as described herein, in some examples.

The foregoing description, for the purpose of explanation, has been described with reference to specific examples or aspects. However, the illustrative discussions above are not intended to be exhaustive or to limit the invention to the precise forms disclosed. For the purpose of clarity and a concise description, features are described herein as part of the same or separate variations; however, it will be appreciated that the scope of the disclosure includes variations having combinations of all or some of the features described. Many modifications and variations are possible in view of the above teachings. The variations were chosen and described in order to best explain the principles of the techniques and their practical applications. Others skilled in the art are thereby enabled to best utilize the techniques and various variations with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A method for clarifying and enhancing intraoperative images, comprising:

receiving one or more intraoperative images depicting a biological tissue and smoke;

inputting the one or more intraoperative images into a trained neural network to obtain a clarified image depicting the biological tissue that is less obscured by smoke than at least one of the one or more received intraoperative images, wherein the trained neural network is trained by:

inputting a simulated training image depicting smoke into the trained neural network to obtain a generated image;

enhancing the generated image to obtain an enhanced generated image;

enhancing a smoke-free training image corresponding to the simulated training image to obtain an enhanced smoke-free training image;

calculating a first loss based on the generated image and the smoke-free training image and a second loss based on the enhanced smoke-free training image and the enhanced generated image; and updating the trained neural network based on the first loss and the second loss;

enhancing, using an equalization algorithm, contrast in the clarified image to obtain an enhanced clarified intraoperative image; and displaying, on a display, the enhanced clarified intraoperative image.

2. The method of claim 1, wherein the received one or more intraoperative images have been captured by an endoscopic camera.

3. The method of claim 1, wherein the received one or more intraoperative images are part of an intraoperative video.

4. The method of claim 1, wherein the trained neural network is a trained convolutional neural network ("CNN").

5. The method of claim 4, wherein the CNN comprises a plurality of layers for optimizing a joint estimation of a transmission map and an atmospheric light in an atmospheric scattering equation.

6. The method of claim 1, wherein the trained neural network is trained using a plurality of smoke-free training images and a plurality of simulated training images depicting smoke.

7. The method of claim 6, wherein each simulated training image is generated by:

receiving a smoke-free training image of the plurality of smoke-free training images;

generating a simulated smoke layer; and aggregating the smoke-free training image and the simulated smoke layer to obtain the simulated training image depicting smoke.

8. The method of claim 7, wherein the simulated smoke layer is generated using Perlin noise.

9. The method of claim 7, wherein aggregating the smoke-free training image and the simulated smoke layer comprises superposing the smoke layer onto the smoke-free image based on a predefined weight.

10. The method of claim 1, wherein:

the trained neural network is trained using artificial images generated using a GAN; and the GAN is trained using real smoky images as a training seed.

11. The method of claim 1, wherein the equalization algorithm is an Adaptive Histogram Equalization algorithm.

12. The method of claim 11, wherein the equalization algorithm is a Contrast Limited Adaptive Histogram Equalization ("CLAHE") algorithm.

13. The method of claim 12, wherein enhancing the clarified image comprises:

converting the clarified image from a RGB color format to a YCbCr color format;

applying the CLAHE algorithm to a Y component of the clarified image; and converting the clarified image from the YCbCr color format to the RGB color format.

14. The method of claim 13, wherein the CLAHE algorithm is applied based on parameters optimized for endoscopic images using heuristics.

15. The method of claim 1, wherein the one or more received intraoperative images are inputted into the trained neural network in accordance with a determination that smoke is detected in the one or more received intraoperative images.

16. The method of claim 15, further comprising: determining a smoke level in the received one or more intraoperative images, wherein the trained neural network is selected based on the determined smoke level.

17. The method of claim 1, further comprising: providing a navigation recommendation based on the enhanced and clarified intraoperative image.

18. A system for clarifying and enhancing intraoperative images, comprising:

one or more processors;

one or more memories; and one or more programs, wherein the one or more programs are stored in the one or more memories and configured to be executed by the one or more processors, the one or more programs including instructions for:

receiving one or more intraoperative images depicting a biological tissue and smoke;

inputting the one or more intraoperative images into a trained neural network to obtain a clarified image depicting the biological tissue that is less obscured by smoke than at least one of the one or more received intraoperative images, wherein the trained neural network is trained by:

inputting a simulated training image depicting smoke into the trained neural network to obtain a generated image;

enhancing the generated image to obtain an enhanced generated image;

enhancing a smoke-free training image corresponding to the simulated training image to obtain an enhanced smoke-free training image;

calculating a first loss based on the generated image and the smoke-free training image and a second loss based on the enhanced smoke-free training image and the enhanced generated image; and updating the trained neural network based on the first loss and the second loss;

enhancing, using an equalization algorithm, contrast in the clarified image to obtain an enhanced clarified intraoperative image; and displaying, on a display, the enhanced clarified intraoperative image.

19. The system of claim 18, wherein the received one or more intraoperative images have been captured by an endoscopic camera.

20. The system of claim 18, wherein the received one or more intraoperative images are part of an intraoperative video.

21. The system of claim 18, wherein the trained neural network is a trained convolutional neural network ("CNN").

22. The system of claim 21, wherein the CNN comprises a plurality of layers for optimizing a joint estimation of a transmission map and an atmospheric light in an atmospheric scattering equation.

23. The system of claim 18, wherein the trained neural network is trained using a plurality of smoke-free training images and a plurality of simulated training images depicting smoke.

24. The system of claim 23, wherein each simulated training image is generated by:

receiving a smoke-free training image of the plurality of smoke-free training images;

generating a simulated smoke layer; and aggregating the smoke-free training image and the simulated smoke layer to obtain the simulated training image depicting smoke.

25. The system of claim 24, wherein the simulated smoke layer is generated using Perlin noise.

26. The system of claim 24, wherein aggregating the smoke-free training image and the simulated smoke layer comprises superposing the smoke layer onto the smoke-free image based on a predefined weight.

27. The system of claim 18, wherein:

the trained neural network is trained using artificial images generated using a GAN; and the GAN is trained using real smoky images as a training seed.

28. The system of claim 18, wherein the equalization algorithm is the Adaptive Histogram Equalization algorithm.

29. The system of claim 28, wherein the equalization algorithm is a Contrast Limited Adaptive Histogram Equalization ("CLAHE") algorithm.

30. The system of claim 29, wherein enhancing the clarified image comprises:

converting the clarified image from a RGB color format to a YCbCr color format;

applying the CLAHE algorithm to the Y component of the clarified image; and converting the clarified image from the YCbCr format to the RGB color format.

31. The system of claim 30, wherein the CLAHE algorithm is applied based on parameters optimized for endoscopic images using heuristics.

32. The system of claim 18, wherein the received one or more intraoperative images are inputted into the trained neural network in accordance with a determination that smoke is detected in the received one or more intraoperative images.

33. The system of claim 32, wherein the one or more programs further include instructions for: determining a smoke level in the received one or more intraoperative images, wherein the trained neural network is selected based on the determined smoke level.

34. The system of claim 18, wherein the one or more programs further include instructions for: providing a navigation recommendation based on the enhanced and clarified intraoperative image.

35. A non-transitory computer-readable storage medium storing one or more programs, the one or more programs comprising instructions, which when executed by one or more processors of an electronic device, cause the electronic device to perform the method of claim 1.

* * * * *